United States Patent
Studer et al.

(10) Patent No.: US 10,858,625 B2
(45) Date of Patent: Dec. 8, 2020

(54) METHODS OF IN VITRO DIFFERENTIATION OF MIDBRAIN DOPAMINE (MPA) NEURONS

(71) Applicant: MEMORIAL SLOAN-KETTERING CANCER CENTER, New York, NY (US)

(72) Inventors: Lorenz Studer, New York, NY (US); Stefan Irion, New York, NY (US); Mark Tomishima, Chatham, NJ (US); Sonja Kriks, San Francisco, CA (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 6 days.

(21) Appl. No.: 15/820,941

(22) Filed: Nov. 22, 2017

(65) Prior Publication Data
US 2018/0094242 A1    Apr. 5, 2018

Related U.S. Application Data

(63) Continuation of application No. PCT/US2016/035312, filed on Jun. 1, 2016.

(60) Provisional application No. 62/169,444, filed on Jun. 1, 2015, provisional application No. 62/169,379, filed on Jun. 1, 2015.

(51) Int. Cl.
| | |
|---|---|
| *A61K 35/30* | (2015.01) |
| *C12N 5/0793* | (2010.01) |
| *A61K 35/545* | (2015.01) |
| *A61P 25/16* | (2006.01) |

(52) U.S. Cl.
CPC ............ *C12N 5/0619* (2013.01); *A61K 35/30* (2013.01); *A61K 35/545* (2013.01); *A61P 25/16* (2018.01); *C12N 2501/13* (2013.01); *C12N 2501/15* (2013.01); *C12N 2501/155* (2013.01); *C12N 2501/41* (2013.01); *C12N 2501/415* (2013.01); *C12N 2501/727* (2013.01); *C12N 2506/02* (2013.01)

(58) Field of Classification Search
CPC .............. C12N 5/0619; C12N 2501/15; C12N 2501/155; C12N 2501/41; C12N 2501/415; C12N 2502/088; C12N 2506/02; C12N 2506/03; A61K 35/545; A61K 35/30
See application file for complete search history.

(56) References Cited

U.S. PATENT DOCUMENTS

| | | |
|---|---|---|
| 6,312,911 B1 | 11/2001 | Bancroft et al. |
| 2008/0268019 A1 | 10/2008 | Badylak et al. |
| 2009/0123433 A1 | 5/2009 | Shroff |
| 2011/0296542 A1 | 12/2011 | Wang et al. |
| 2015/0010514 A1 | 1/2015 | Studer et al. |
| 2015/0159135 A1 | 6/2015 | Davis et al. |

FOREIGN PATENT DOCUMENTS

| | | |
|---|---|---|
| WO | WO 2006/071778 A2 | 7/2006 |
| WO | WO 2010/096496 A2 | 8/2010 |
| WO | WO 2011/149762 A2 | 12/2011 |
| WO | WO 2013/067362 A1 | 5/2013 |
| WO | WO 2014/176606 A1 | 10/2014 |
| WO | WO 2015/034012 A1 | 3/2015 |
| WO | WO 2015/077648 A1 | 5/2015 |
| WO | WO 2015/143342 A1 | 9/2015 |

OTHER PUBLICATIONS

Arenas et al., "How to make a midbrain dopaminergic neuron," Development, 142(11):1918-1936 (2015).
Cadigan et al., "Wnt signaling: complexity at the surface," J Cell Sci. 119:395-402 (2006).
Calder et al., "Retinoic Acid-Mediated Regulation of GLI3 Enables Efficient Motoneuron Derivation from Human ESCs in the Absence of Extrinsic SHH Activation," J Neurosci. 35(33):11462-11481 (2015).
Chambers et al., "Combined small-molecule inhibition accelerates developmental timing and converts human pluripotent stem cells into nociceptors," Nat Biotechnol. 30(7):715-720 (2012).
Chambers et al., "Highly efficient neural conversion of human ES and iPS cells by dual inhibition of SMAD signaling," Nat Biotechnol. 27(3):275-280 (2009).
Chen et al., "Chemically defined conditions for human iPSC derivation and culture," Nat Methods 8(5):424-429 (2011).
Cuny et al., "Structure-activity relationship study of bone morphogenetic protein (BMP) signaling inhibitors," Bioorg. Med. Chem. Lett. 18:4388-4392 (2008).
Doble et al., "GSK-3: tricks of the trade for a multi-tasking kinase," J Cell Sci. 116:1175-1186 (2003).
Extended European Search Report dated Oct. 2, 2018 in EP Application No. 16804350.
Fasano et al., "Efficient Derivation of Functional Floor Plate Tissue from Human Embryonic Stem Cells," Cell Stem Cell, 6(4):336-347 (2010).
International Search Report dated Aug. 29, 2016 in International Application No. PCT/US16/35312.

(Continued)

*Primary Examiner* — Robert C Hayes
(74) *Attorney, Agent, or Firm* — Baker Botts L.L.P.

(57) ABSTRACT

The presently disclosed subject matter provides for in vitro methods of inducing differentiation of human stem cells into midbrain dopamine neurons, and precursors thereof, and cells generated by such methods. The presently disclosed subject matter also provides for uses of such cells for treating neurodegenerative disorders.

28 Claims, 22 Drawing Sheets

(56) References Cited

OTHER PUBLICATIONS

Figure 1:
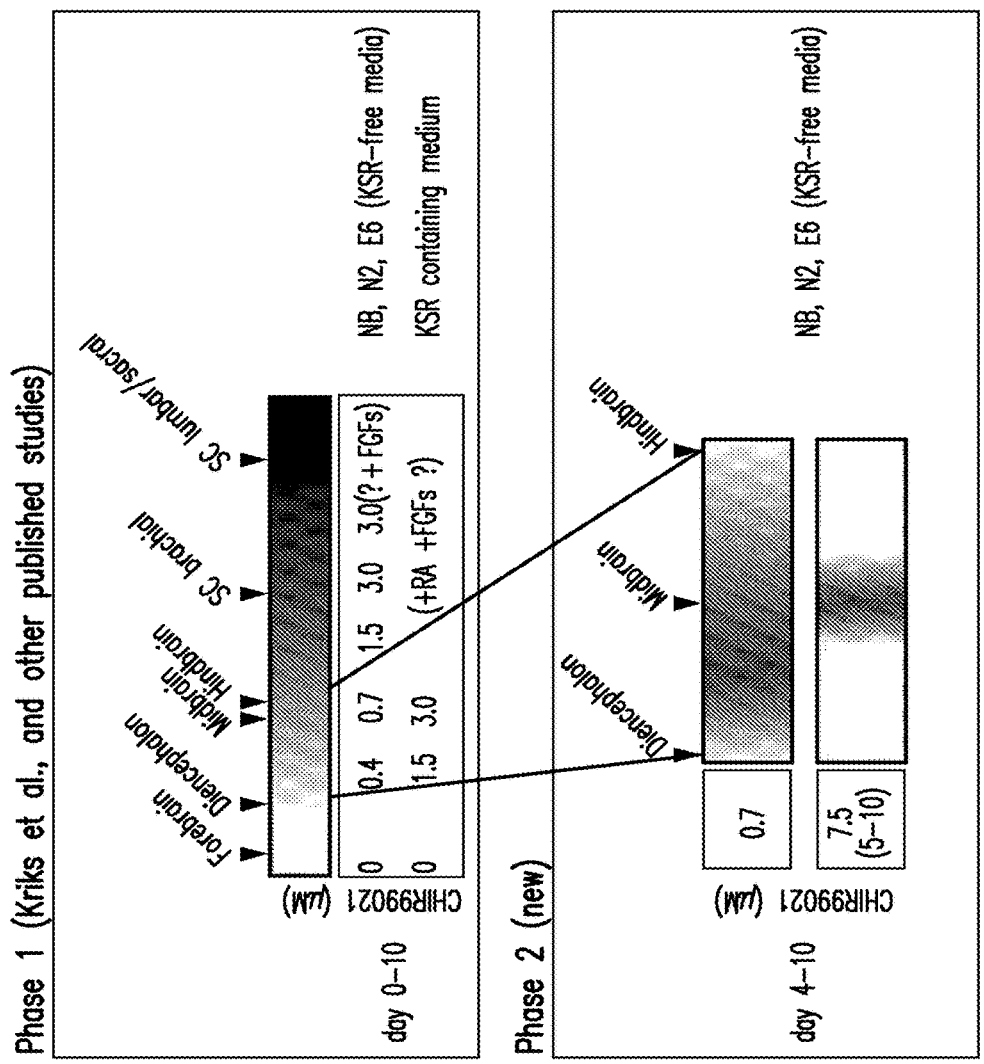

Kikuchi, et al., "Multiplicity of the interactions of Wnt proteins and their receptors," Cell Signaling. 19:659-671 (2007).
Kriks et al., "Dopamine neurons derived from human ES cells efficiently engraft in animal models of Parkinson's disease," Nature 480(7378):547-551 (2011).
Yu et al., "BMP type I receptor inhibition reduces heterotopic ossification," Nat Med 14:1363-1369 (2008).

| Gene Symbol | 012014 BD TESR D0 | 012014 BD Feeders D0 | 012014 BD EB D0 | 112213 MT EB D13 | 031914 BD EB D13 | -FGF8 DATE UNK CDI D26 | +FGF8 Dopaneurons DATE UNK CDI D38 | +FGF8 Dopaneurons DATE UNK CDI D33 |
|---|---|---|---|---|---|---|---|---|
| NEUROG2 | 36.34 | 34.15 | 36.00 | 26.01 | 31.50 | 20.10 | 30.23 | 31.80 |
| TH | 32.21 | 33.44 | 32.80 | 24.93 | 29.00 | 22.78 | 21.77 | 21.85 |
| SLC18A2 | 30.79 | 29.00 | 31.44 | 27.68 | 32.60 | 26.78 | 27.75 | 25.37 |
| KCNJ6 | 30.41 | 28.72 | 30.16 | 28.93 | 28.24 | 22.97 | 24.21 | 24.00 |
| POU4F1 | 31.65 | 28.61 | 32.19 | 28.36 | 29.76 | 23.53 | 23.18 | 22.73 |
| NKX6-1 | 31.28 | 29.61 | 32.83 | 22.66 | 24.70 | 22.58 | 21.97 | 20.96 |
| SIM1 | 31.24 | 34.04 | 36.00 | 27.34 | 27.41 | 24.41 | 29.88 | 27.52 |
| NKX2-1 | 34.40 | 36.00 | 36.00 | 20.99 | 23.97 | 29.24 | 28.65 | 36.00 |
| FEV | 36.00 | 36.00 | 36.00 | 36.00 | 36.00 | 36.00 | 36.00 | 36.00 |
| FABP7 | 32.53 | 36.00 | 35.99 | 31.20 | 32.35 | 32.02 | 30.53 | 29.75 |
| NKX2-2 | 30.63 | 31.94 | 34.23 | 28.08 | 31.09 | 31.04 | 31.97 | 31.75 |
| SLC17A6 | 30.54 | 32.96 | 34.67 | 28.70 | 28.16 | 20.69 | 22.01 | 21.27 |
| POU5F1 | 21.18 | 20.87 | 21.98 | 26.07 | 29.87 | 28.26 | 29.62 | 28.61 |
| PAX6 | 30.77 | 30.36 | 31.73 | 29.30 | 29.21 | 26.82 | 30.82 | 26.09 |
| KRT19 | 22.11 | 21.90 | 22.83 | 22.92 | 24.15 | 24.86 | 29.55 | 28.15 |
| MKI67 | 22.62 | 22.34 | 23.19 | 21.13 | 23.91 | 23.16 | 29.72 | 32.17 |
| TOP2A | 21.78 | 21.54 | 22.37 | 19.37 | 21.82 | 22.75 | 28.62 | 29.80 |
| CORIN | 32.85 | 34.00 | 37.78 | 29.24 | 24.04 | 25.95 | 27.20 | 27.22 |
| OTX2 | 21.85 | 21.59 | 21.68 | 16.78 | 19.47 | 22.65 | 23.76 | 23.10 |
| GBX2 | 25.74 | 26.64 | 25.28 | 28.01 | 32.10 | 26.11 | 28.24 | 27.39 |
| FOXA2 | 31.04 | 31.09 | 31.59 | 20.30 | 22.66 | 22.48 | 23.09 | 22.79 |
| LMX1A | 30.78 | 30.25 | 28.88 | 19.77 | 19.92 | 20.85 | 21.36 | 20.82 |
| LMX1B | 32.33 | 29.85 | 32.41 | 21.05 | 22.47 | 22.01 | 21.52 | 21.04 |
| ASCL1 | 31.06 | 31.84 | 30.01 | 23.84 | 24.29 | 23.47 | 29.77 | 28.58 |

FIG. 4

| FGFB DATE UNK CD1 D35 | 021714 SK EB D25 | 021814 SK EB D25 | 102313 WT ??? D25 | JWS D50 |
|---|---|---|---|---|
| 28.03 | 20.00 | 28.60 | 33.36 | 20.60 |
| 22.43 | 23.86 | 23.76 | 22.94 | 20.95 |
| 28.07 | 28.32 | 27.78 | 27.01 | 24.92 |
| 24.23 | 26.12 | 24.89 | 23.89 | 22.74 |
| 25.06 | 22.81 | 28.29 | 26.02 | 25.99 |
| 25.03 | 23.31 | 24.70 | 25.89 | 24.21 |
| 27.61 | 25.50 | 26.42 | 28.06 | 29.19 |
| 28.16 | 33.06 | 29.51 | 27.55 | 36.00 |
| 40.24 | 36.00 | 36.00 | 36.47 | 36.00 |
| 32.27 | 34.58 | 35.05 | 33.86 | 30.81 |
| 32.41 | 29.00 | 27.57 | 28.48 | 31.37 |
| 21.28 | 22.09 | 23.77 | 24.18 | 20.64 |
| 30.47 | 31.94 | 30.69 | 31.13 | 27.66 |
| 28.91 | 29.27 | 30.91 | 29.66 | 27.02 |
| 27.44 | 27.09 | 23.79 | 23.86 | 28.07 |
| 25.93 | 25.01 | 25.51 | 24.94 | 28.75 |
| 24.92 | 23.21 | 24.71 | 24.02 | 26.91 |
| 28.57 | 21.96 | 23.43 | 24.88 | 25.76 |
| 22.57 | 22.79 | 21.22 | 20.43 | 25.86 |
| 28.22 | 28.63 | 31.93 | 31.40 | 28.90 |
| 23.48 | 22.53 | 22.37 | 23.65 | 22.85 |
| 21.29 | 20.97 | 20.25 | 20.25 | 20.89 |
| 22.43 | 22.83 | 22.28 | 22.51 | 22.15 |
| 24.27 | 24.38 | 20.99 | 21.23 | 27.01 |

FIG. 4 (continued)

| Gene Symbol | 012014 BD TESR D0 | 012014 BD Feeders D0 | 012014 BD EB D0 | 1/22/13 MT EB D13 | 03/19/14 BD EB D13 | -FGF8 DATE UNK CD1 D26 | +FGF8 Dopaneurons DATE UNK DC1 D38 | +FGF8 Dopaneurons DATE UNK DC1 D33 |
|---|---|---|---|---|---|---|---|---|
| PITX3 | 34.14 | 32.16 | 35.25 | 28.92 | 31.87 | 30.95 | 28.95 | 29.47 |
| NR4A2 | 28.87 | 28.73 | 29.94 | 25.13 | 27.42 | 20.57 | 22.67 | 22.10 |
| CHRNB3 | 34.18 | 36.00 | 35.29 | 30.96 | 36.00 | 23.77 | 25.00 | 24.74 |
| DDC | 32.27 | 34.10 | 34.66 | 23.18 | 25.51 | 21.53 | 20.65 | 20.33 |
| CCK | 28.81 | 28.83 | 30.74 | 20.43 | 24.79 | 24.19 | 24.74 | 25.35 |
| DRD2 | 29.10 | 29.96 | 30.36 | 24.30 | 29.04 | 24.17 | 26.20 | 25.82 |
| DBH | 29.85 | 30.16 | 30.41 | 25.37 | 26.96 | 28.26 | 29.67 | 29.36 |
| ISL1 | 32.48 | 30.74 | 34.80 | 29.29 | 30.06 | 28.73 | 30.00 | 26.99 |
| EN1 | 33.14 | 31.99 | 38.75 | 37.21 | 34.00 | 20.90 | 27.44 | 27.02 |
| FOXG1 | 27.72 | 28.14 | 28.81 | 36.00 | 36.00 | 33.87 | 36.00 | 36.00 |
| HOXB2 | 29.77 | 28.75 | 36.36 | 30.16 | 28.89 | 35.92 | 31.08 | 32.35 |
| DLX2 | 30.78 | 29.73 | 33.08 | 27.21 | 30.29 | 29.70 | 30.57 | 30.28 |
| GATA3 | 32.61 | 31.39 | 33.53 | 28.54 | 30.35 | 32.29 | 36.00 | 29.60 |
| PHOX2A | 31.40 | 29.33 | 30.38 | 22.54 | 26.84 | 34.61 | 31.09 | 29.80 |
| PHOX2B | 33.29 | 35.96 | 34.38 | 29.30 | 32.30 | 33.27 | 31.18 | 28.36 |
| PAX6 | 25.72 | 26.62 | 27.75 | 26.37 | 28.24 | 29.41 | 36.00 | 31.77 |
| GFAP | 35.55 | 31.94 | 33.65 | 36.00 | 33.70 | 33.50 | 34.52 | 34.82 |
| MAP2 | 24.51 | 26.64 | 24.67 | 20.56 | 21.66 | 19.47 | 19.20 | 19.95 |
| SHH | 33.70 | 33.70 | 38.81 | 22.68 | 22.70 | 25.04 | 25.54 | 26.39 |
| ACTB | 15.50 | 15.50 | 15.50 | 15.50 | 15.50 | 15.50 | 15.50 | 15.50 |
| GAPDH | 16.94 | 16.92 | 17.05 | 14.68 | 17.94 | 17.32 | 17.92 | 17.38 |
| HGDC | 33.98 | 35.40 | 37.56 | 31.37 | 36.00 | 35.43 | 36.00 | 32.85 |
| RTC | 21.04 | 21.06 | 22.16 | 21.14 | 21.10 | 22.27 | 18.57 | 22.11 |
| PPC | 20.64 | 19.18 | 21.43 | 17.27 | 20.77 | 18.35 | 17.85 | 17.96 |

FIG. 4 (continued)

| FGFB DATE UNK CD1 D35 | 021714 SK EB D25 | 021814 SK EB D23 | 102313 MT ??? D25 | JWS D50 |
|---|---|---|---|---|
| 30.75 | 29.64 | 27.11 | 26.55 | 29.81 |
| 21.25 | 21.48 | 23.42 | 22.05 | 20.54 |
| 24.16 | 25.72 | 31.35 | 27.39 | 24.77 |
| 22.04 | 22.13 | 21.93 | 23.17 | 21.50 |
| 22.50 | 28.44 | 25.28 | 26.18 | 22.58 |
| 24.85 | 24.10 | 23.85 | 22.84 | 22.76 |
| 30.55 | 28.17 | 29.88 | 28.31 | 27.78 |
| 32.75 | 28.43 | 30.41 | 28.85 | 29.71 |
| 31.75 | 33.24 | 33.38 | 32.85 | 29.06 |
| 33.54 | 33.48 | 35.66 | 32.35 | 32.69 |
| 34.23 | 29.96 | 28.11 | 28.91 | 30.66 |
| 31.47 | 30.04 | 31.09 | 28.79 | 29.73 |
| 33.41 | 33.16 | 36.26 | 32.84 | 33.35 |
| 35.80 | 30.72 | 30.19 | 29.92 | 32.14 |
| 35.20 | 29.44 | 32.77 | 33.09 | 32.04 |
| 31.75 | 28.50 | 30.08 | 28.05 | 27.86 |
| 33.91 | 34.87 | 37.79 | 34.05 | 33.15 |
| 19.09 | 23.28 | 22.41 | 21.18 | 20.05 |
| 24.07 | 21.99 | 22.80 | 24.56 | 25.93 |
| 15.50 | 15.50 | 15.50 | 15.50 | 15.50 |
| 17.35 | 17.02 | 17.69 | 17.83 | 16.71 |
| 34.80 | 36.63 | 36.00 | 36.18 | 36.00 |
| 21.40 | 22.86 | 25.56 | 22.13 | 21.05 |
| 19.96 | 19.82 | 19.90 | 22.98 | 17.90 |

FIG. 4 (continued)

Gene expression panel

Engrailed <23 cycles
GBX2 >30 cycles
PAX6 >30 cycles
NKX2.1 >30 cycles

METHODS OF IN VITRO DIFFERENTIATION OF MIDBRAIN DOPAMINE (MPA) NEURONS

CROSS REFERENCE TO RELATED APPLICATIONS

This application is a Continuation of International Patent Application No. PCT/US2016/035312 filed Jun. 1, 2016, which claims priority to U.S. Provisional Application No. 62/169,379 filed Jun. 1, 2015, and U.S. Provisional Application No. 62/169,444 filed Jun. 1, 2015, priority to each of which is claimed, and the contents of each of which are incorporated by reference in their entireties herein.

1. INTRODUCTION

The presently disclosed subject matter relates to midbrain dopamine (DA) neurons, and precursors thereof, derived from human stem cells, and uses thereof for cell-based treatment of neurological disorders.

2. BACKGROUND OF THE INVENTION

Previously, embryonic and somatic stem cells were used as therapeutics and model systems for neurodegenerative diseases. Research and technological developments relating to directed differentiation of embryonic and somatic stem cells has taken place in the field of diseases of the central nervous system (CNS), such as for Huntington's, Alzheimer's, Parkinson's, and multiple sclerosis. However the results of these studies showed little in vivo capability to restore neuronal function and often resulted in the growth of unwanted tumors in the patients.

Therefore there is a need for compositions and methods for differentiating neuronal progenitor cells to be used in treating neurodegenerative disorders such as Parkinson's disease.

3. SUMMARY OF THE INVENTION

The presently disclosed subject matter relates to midbrain dopamine (DA) neurons (mDA), and precursors thereof, derived from human stem cells at least in part by in vitro differentiation.

The presently disclosed subject matter relates to the discovery that midbrain dopamine (DA) neurons, and precursors thereof, can be differentiated from human stem cells by dual inhibition of SMAD signaling (for example, by inhibition of TGFβ/Activin-Nodal signaling and BMP signaling), along with the activation of Sonic Hedgehog (SHH) signaling, and activation of wingless (Wnt) signaling, wherein the concentration of a Wnt activating compound is increased about 4 days after initial contact of the cells to the SMAD inhibitors, SHH activator, and Wnt activator. In certain embodiments, the presently disclosed methods provide for advantages over methods of differentiating stem cells into midbrain DA cells that do not comprise an increase of a Wnt activating compound, for example, by reducing the expression of markers of immature progenitor cells, for example, PAX6, and producing cells that differentiate into functional Tyrosine Hydroxylase expressing mDA cells following engraftment.

In certain embodiments, the cells are further contacted with DA neuron lineage activators and inhibitors, for example, brain-derived neurotrophic factor (BDNF), glial cell-derived neurotrophic factor (GDNF), Cyclic adenosine monophosphate (cAMP), Transforming growth factor beta (TGFβ, for example, TGFβ3), ascorbic acid (AA), and DAPT (which is also known as, N-[(3,5-Difluorophenyl)acetyl]-L-alanyl-2-phenyl]glycine-1,1-dimethylethyl ester; LY-374973, N-[N-(3,5-Difluorophenacetyl)-L-alanyl]-S-phenylglycine t-butyl ester; or N-[N-(3,5-difluorophenacetyl)-L-alanyl]-S-phenylglycine t-butyl ester).

In certain embodiments, the presently disclosed subject matter provides for in vitro methods for inducing differentiation of human stem cells into midbrain DA precursors comprising contacting a population or plurality of human stem cells with one or more inhibitor of TGFβ/Activin-Nodal signaling (i.e., a first SMAD inhibitor), one or more inhibitor of BMP signaling (i.e., a second SMAD inhibitor), one or more activator of wingless (Wnt) signaling, and one or more activator of Sonic Hedgehog (SHH) signaling. In certain embodiments, the inhibitors and activators are contacted to the cells concurrently. In certain embodiments, the concentration of the activator of Wnt signaling is increased at least about 2, 3, 4, 5 or 6 days after the cells are initially contacted with the Wnt activator. In certain embodiments, the cells are contacted with the increased concentration of the Wnt activator for at least about 4, 5, 6, 7, 8, 9, or 10 days or more.

In certain embodiments, the cells are contacted with the foregoing agents in amounts effective to increase detectable levels of expression of one or more markers of midbrain DA neurons, or precursors thereof, for example, but not limited to, engrailed-1 (EN-1), orthodenticle homeobox 2 (OTX2), tyrosine hydroxylase (TH), nuclear receptor related-1 protein (NURR1), forkhead box protein A2 (FOXA2), and LIM homeobox transcription factor 1 alpha (LMX1A).

In certain embodiments, the cells are contacted with the foregoing agents in amounts effective to increase detectable levels of expression of one or more of neuron-specific class III beta-tubulin (Tuj1), Trefoil factor family 3 (TTF3), paired-like homeodomain 3 (PITX3), achaete-scute complex (ASCL), early B-cell factor 1 (EBF-1), early B-cell factor 3 (EBF-3), transthyretin (TTR), synapsin, dopamine transporter (DAT), and G-protein coupled, inwardly rectifying potassium channel (Kir3.2/GIRK2), CD142, DCSM1, CD63 and/or CD99.

The present disclosure also provides for a population of in vitro differentiated cells expressing one or more marker of midbrain DA cells, or precursors thereof, prepared according to the methods described herein. In certain embodiments, the differentiated cell population is derived from a population of human stem cells. The presently disclosed subject matter further provides for compositions comprising such a differentiated cell population.

In certain embodiments, the cells are cultured with the foregoing agents in amounts effective to decrease detectable levels of expression of paired box protein (PAX6) and/or Ki67. In certain embodiments, the cells do not express detectable levels of PAX6 and/or Ki67.

In certain embodiments, the cells prepared according to the methods described herein can be sorted, selected and isolated based on CD142 expression, and/or cholinergic receptor (CHRNB3) expression, for example, using flow cytometry.

In certain embodiments, the cells prepared according to the methods described herein can be further contacted with a polysialyltransferase, for example, a bacterial polysialyltransferase, such as *Neisseria meningitidis* polysialyltransferase (PST$_{Nm}$). In certain embodiments, the cells are recombinant cells expressing a recombinant polysialyltransferase.

Furthermore, the presently disclosed subject matter provides for kits for inducing differentiation of stem cells.

In certain embodiments, the kit comprises (a) one or more inhibitor of transforming growth factor beta (TGFβ)/Activin-Nodal signaling (i.e., a first SMAD inhibitor), (b) one or more inhibitor of bone morphogenetic proteins (BMP) signaling (i.e., a second SMAD inhibitor), (c) one or more activator of wingless (Wnt) signaling, (d) one or more activator of Sonic Hedgehog (SHH) signaling, and (e) instructions for inducing differentiation of stem cells into a population of differentiated cells that express one or more marker of midbrain DA neurons, or precursors thereof.

In certain embodiments, the present disclosure provides for kits comprising the stem cell-derived precursors prepared according to the methods described herein. In certain embodiments, the stem cell-derived cells are mature, differentiated cells, for example, midbrain DA cells.

In certain embodiments, said one or more inhibitor of TGFβ/Activin-Nodal signaling is a small molecule selected from the group consisting of SB431542, derivatives thereof, and mixtures thereof. In certain embodiments, said one or more inhibitor of BMP signaling is a small molecule selected from the group consisting of LDN193189, derivatives thereof, and mixtures thereof. In certain embodiments, said one or more activator of Wnt signaling lowers glycogen synthase kinase 3β (GSK3β) for activation of Wnt signaling. In certain embodiments, said one or more activator of Wnt signaling is a small molecule selected from the group consisting of CHIR99021, WNT3A, derivatives thereof, and mixtures thereof. In certain embodiments, the activator of SHH signaling is selected from the group consisting of recombinant SHH, purified SHH, C25II, and smoothened (SMO) receptor agonists such as the small molecule purmorphamine, derivatives thereof, and mixtures thereof.

In certain embodiments, said human stem cells are selected from the group consisting of human embryonic stem cells, human induced pluripotent stem cells, human parthenogenetic stem cells, primordial germ cell-like pluripotent stem cells, epiblast stem cells, and F-class pluripotent stem cells. Human induced pluripotent stem cells (iPSC) are cells prepared from more differentiated cells, for example, a differentiated somatic cell, formed by the introduction of embryonic genes (such as but not limited to OCT4, SOX2, cMyc, and KLF4 transgenes) into the somatic cell (see, for example, Takahashi and Yamanaka, Cell 126, 663-676 (2006), herein incorporated by reference).

In certain embodiments, the method further comprises subjecting said population of differentiated cells to conditions favoring maturation of said differentiated cells into a population of midbrain DA neurons.

The presently disclosed subject matter further provides for methods of treating a neurodegenerative disorder in a subject, for example, Parkinson's disease. In certain embodiments, the method comprises administering an effective amount of the differentiated cell population described herein into a subject suffering from a neurodegenerative disorder.

The presently disclosed subject matter further provides for a differentiated cell population described herein for treating a neurodegenerative disorder.

The presently disclosed subject matter further provides for uses of the differentiated cell population described herein in the manufacture of a medicament for treating a neurodegenerative disorder.

The foregoing has outlined rather broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

4. BRIEF DESCRIPTION OF THE FIGURES

FIG. 1 shows that differentiating hESCs for 10 days according to the method described by Kriks et al., Nature. 2011 Nov. 6; 480(7378):547-51 in KSR media (Non-GMP) or in E8/NB/N2 media (GMP V1) without a Wnt bump produced midbrain DA neurons as well as neurons of other brain regions. Culturing hESCs in E8/NB/N2 media according to the methods Example 1 utilizing a 7.5 μM (or 5-10 μM) Wnt bump at D4-D10 was specific for producing midbrain DA cells.

Figure 2:
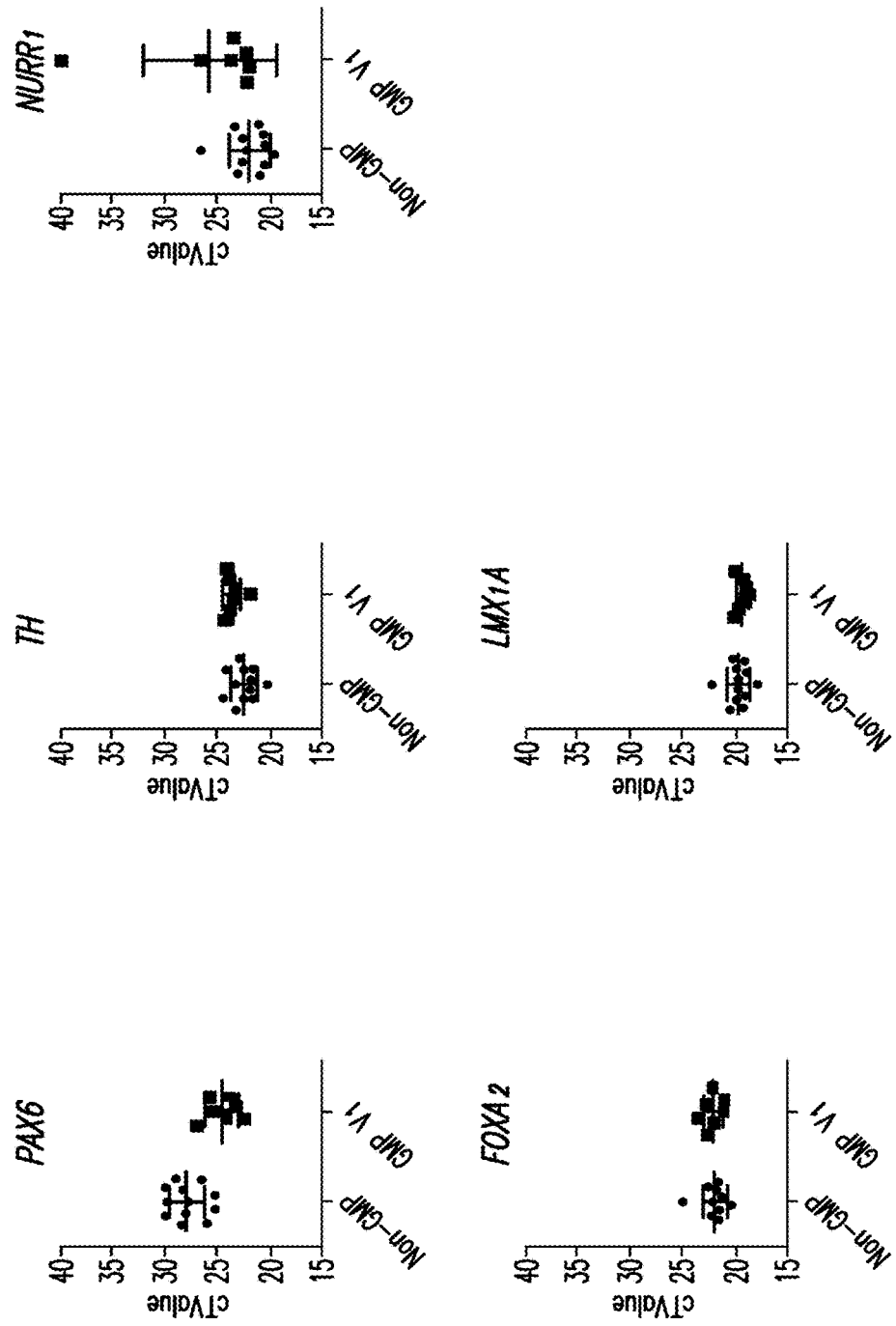

FIG. 2 shows expression of PAX6, TH, NURR1, FOXA2, and LMX1A in hESCs differentiated between 22 and 27 days according to the method described by Kriks et al., Nature. 2011 Nov. 6; 480(7378):547-51 in KSR media (Non-GMP) or in E8/NB/N2 media (GMP V1) without a Wnt bump. Cells were harvested and analyzed by qRT-PCR for the indicated genes (n=between 3 and 14 per condition). Data is represented as normalized cT values, with lower numbers indicating higher gene expression.

Figure 3:
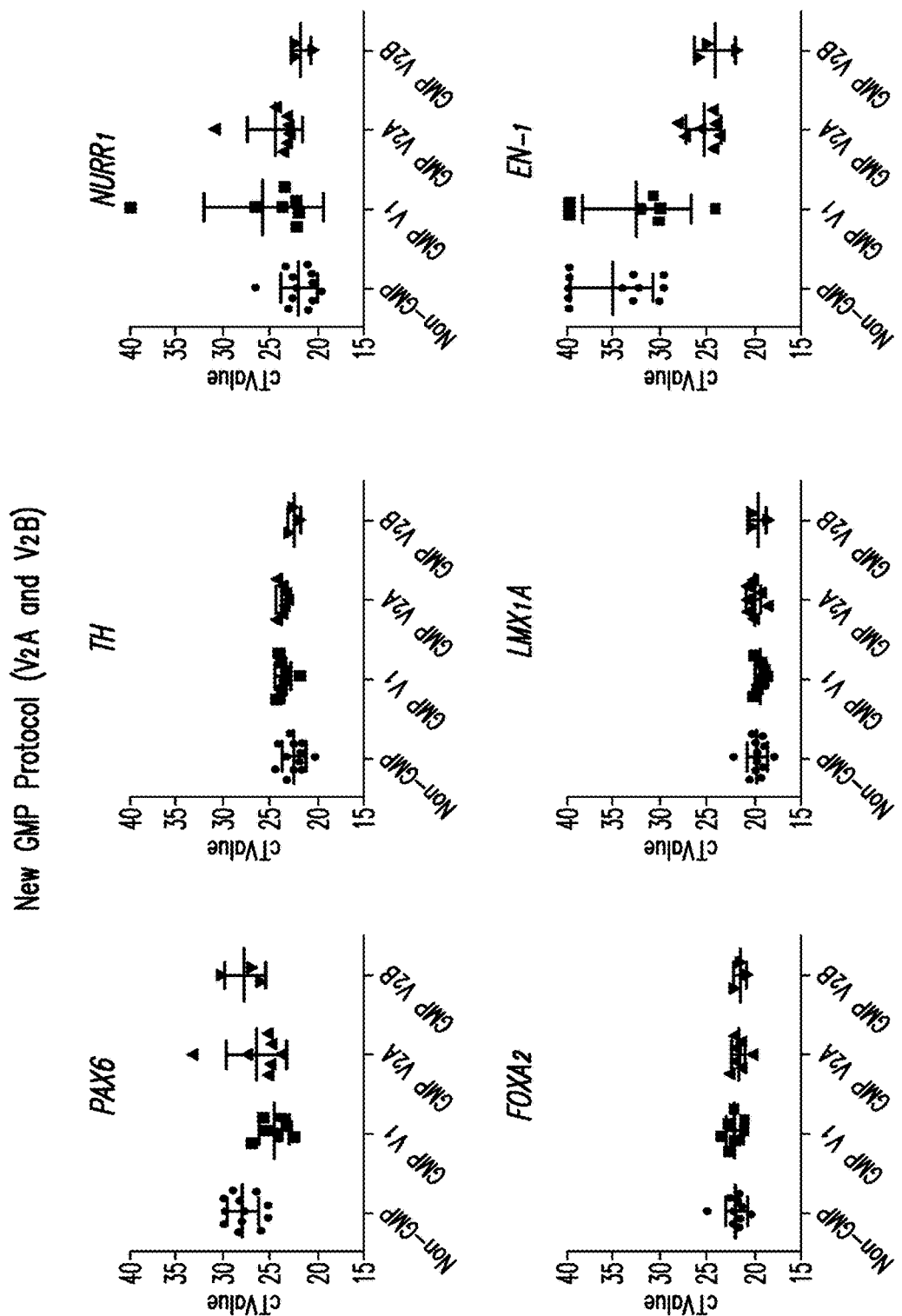

FIG. 3 shows expression of PAX6, TH, NURR1, FOXA2, LMX1A, and En-1 in hESCs differentiated between 22 and 27 days according to the method described by Kriks et al., Nature. 2011 Nov. 6; 480(7378):547-51 in KSR media (Non-GMP) or in E8/NB/N2 media (GMP V1) without a Wnt bump, and according to the methods described by Example 1, which includes culturing the hESCs in E8/NB/N2 media with a 3 μM (GMP V2A) or 7.5 μM (GMP V2B) Wnt bump. Cells were harvested and analyzed by qRT-PCR for the indicated genes (n=between 3 and 14 per condition). Data is represented as normalized cT values, with lower numbers indicating higher gene expression. Cells cultured according to GMP V2A and GMP V2B expressed higher levels of En-1.

FIG. 4 shows midbrain DA markers that can be used to identify differentiated midbrain DA cells.

Figure 5:
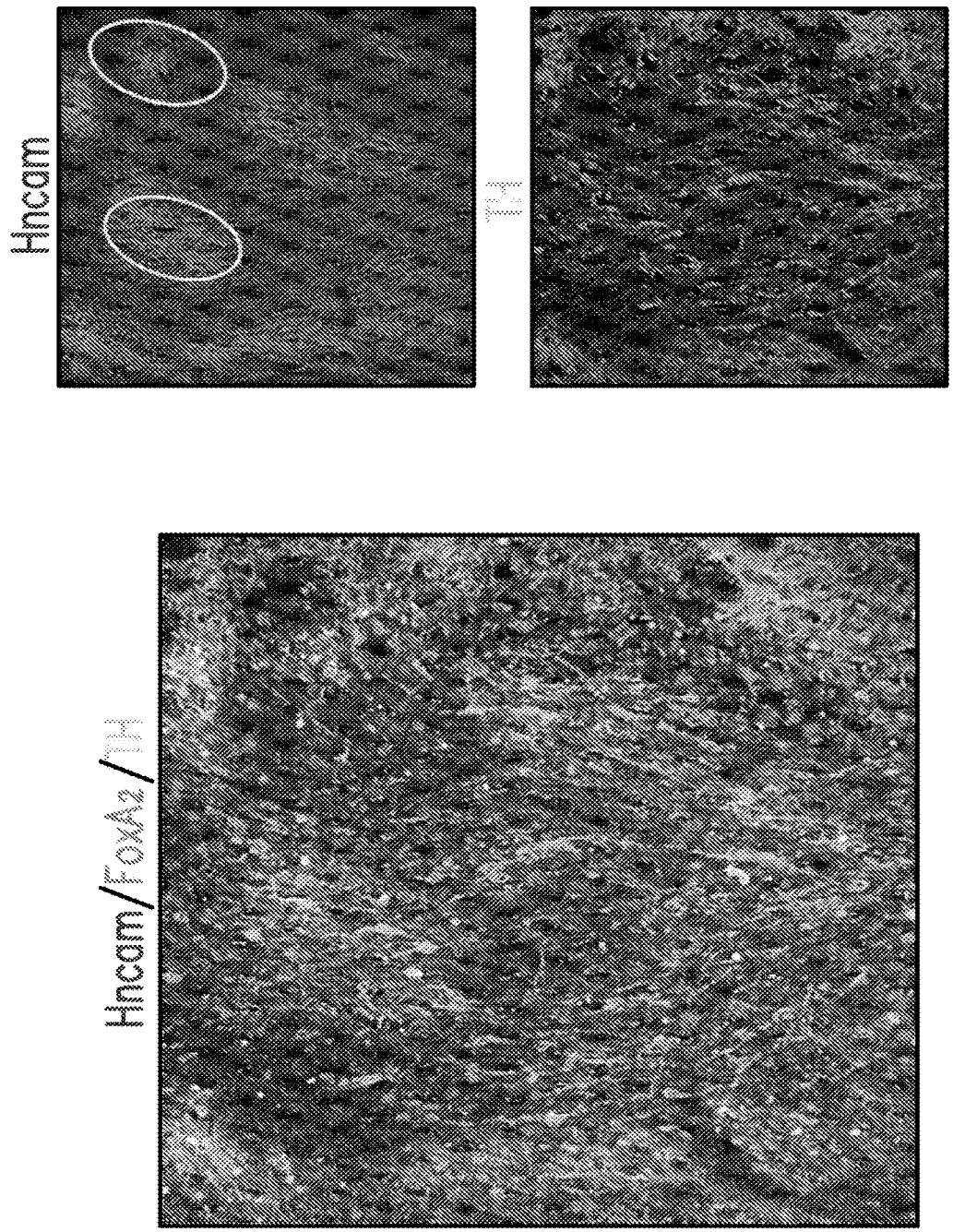

FIG. 5 shows that hESCs maintained under E8/matrigel conditions and then differentiated for 25 days according to the method described by Kriks et al., Nature. 2011 Nov. 6; 480(7378):547-51 in NB/N2 media with 0.7 μM Wnt, without a Wnt bump, exhibit areas of proliferation in vivo. Following differentiation, cells were transplanted into unlesioned, immunocompromised mice and grafts were harvested after 4 weeks. Sections were analyzed by ICC for human NCAM, FOXA2 and TH. While many TH+ cells expressing FOXA2 were observed, clusters of hNCAM+ cells within the graft core were also detected. These patches also expressed PAX6, indicating neural progenitor status.

Figure 6A:
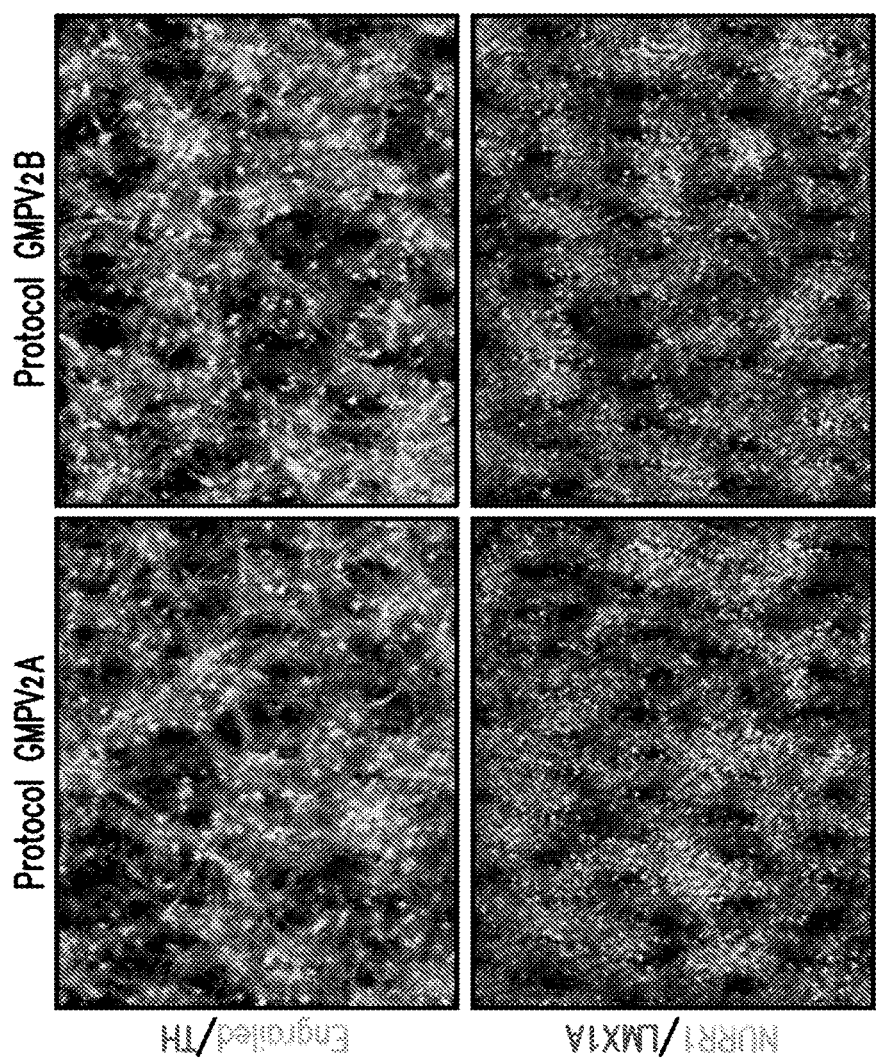
Figure 6B:
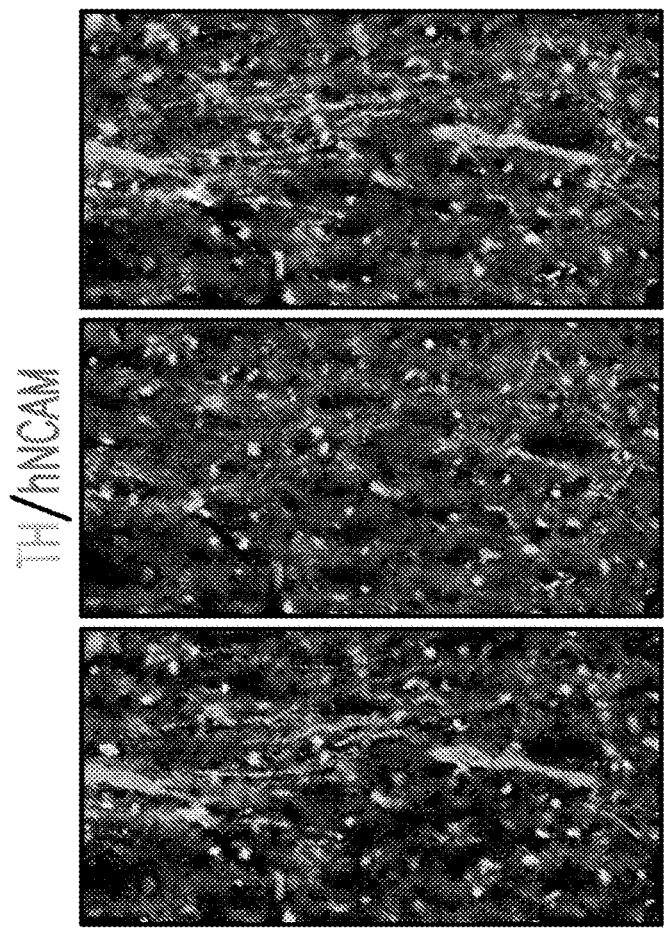
Figure 6B:
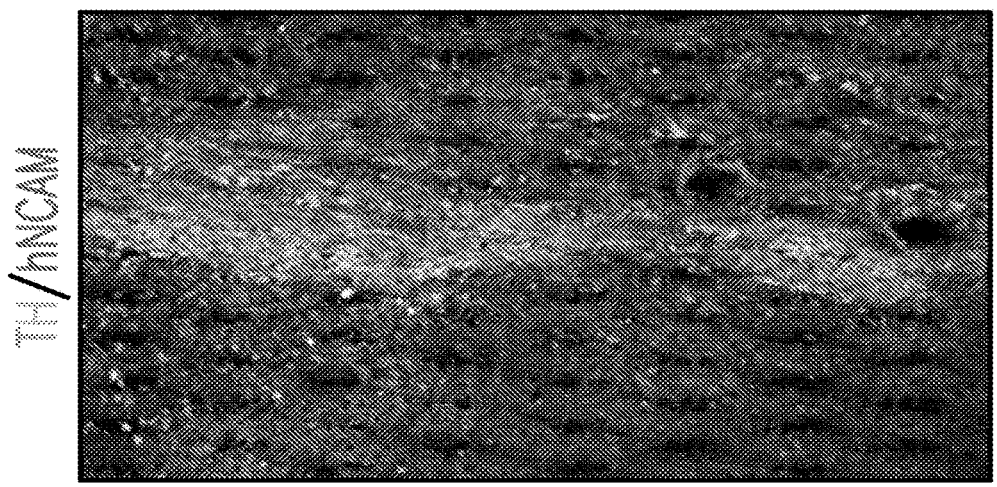

FIG. 6A-B shows (A) that hESCs maintained under E8/matrigel conditions and then differentiated for 25 days in NB/N2 media according to the GMP V2A (3 μM Wnt bump in the presence of a 0.7 μM Wnt background) and GMP V2B (7.5 µM Wnt bump in the presence of a 0.7 µM Wnt background) culture methods described by Example 1, induced differentiation of midbrain DA cells expressing high levels of EN-1 and TH. Midbrain DA neurons were fixed and stained for TH and EN-1 in vitro (upper panels) and NURR1 and LMX1A (lower panel). (B) Midbrain DA cells differentiated according to the GMP V2B protocol were transplanted into the striatum of unlesioned, immunocompromised mice, and exhibited enhanced fiber outgrowth and expression of hNCAM and TH 3-weeks post grafting.

Figure 7:
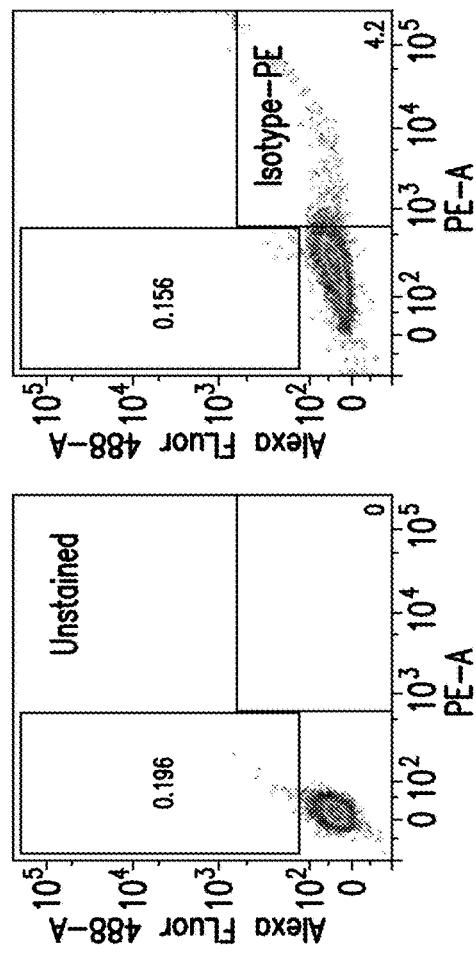
Figure 7:
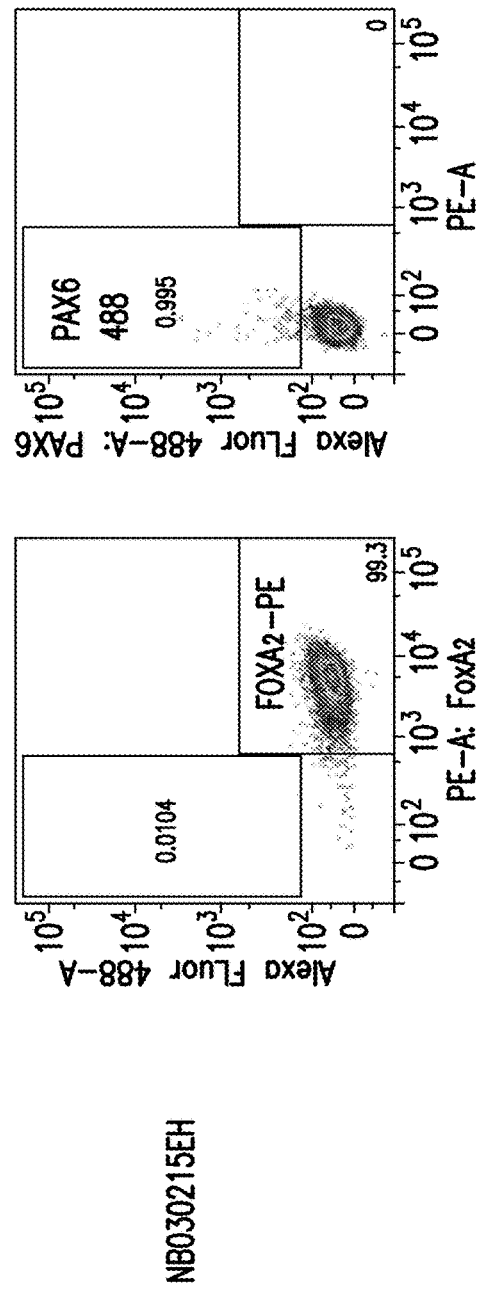

FIG. 7 shows that hESCs maintained under E8/matrigel conditions and then differentiated for 25 days in NB/N2 media according to the GMP V2B (7.5 µM Wnt bump in the presence of a 0.7 Wnt background) culture method described by Example 1, eliminated PAX6 expressing cells while maintaining FOXA2 expressing cells. Cells were harvested and analyzed by flow cytometry for the presence of FOXA2 and PAX6.

Figure 8:
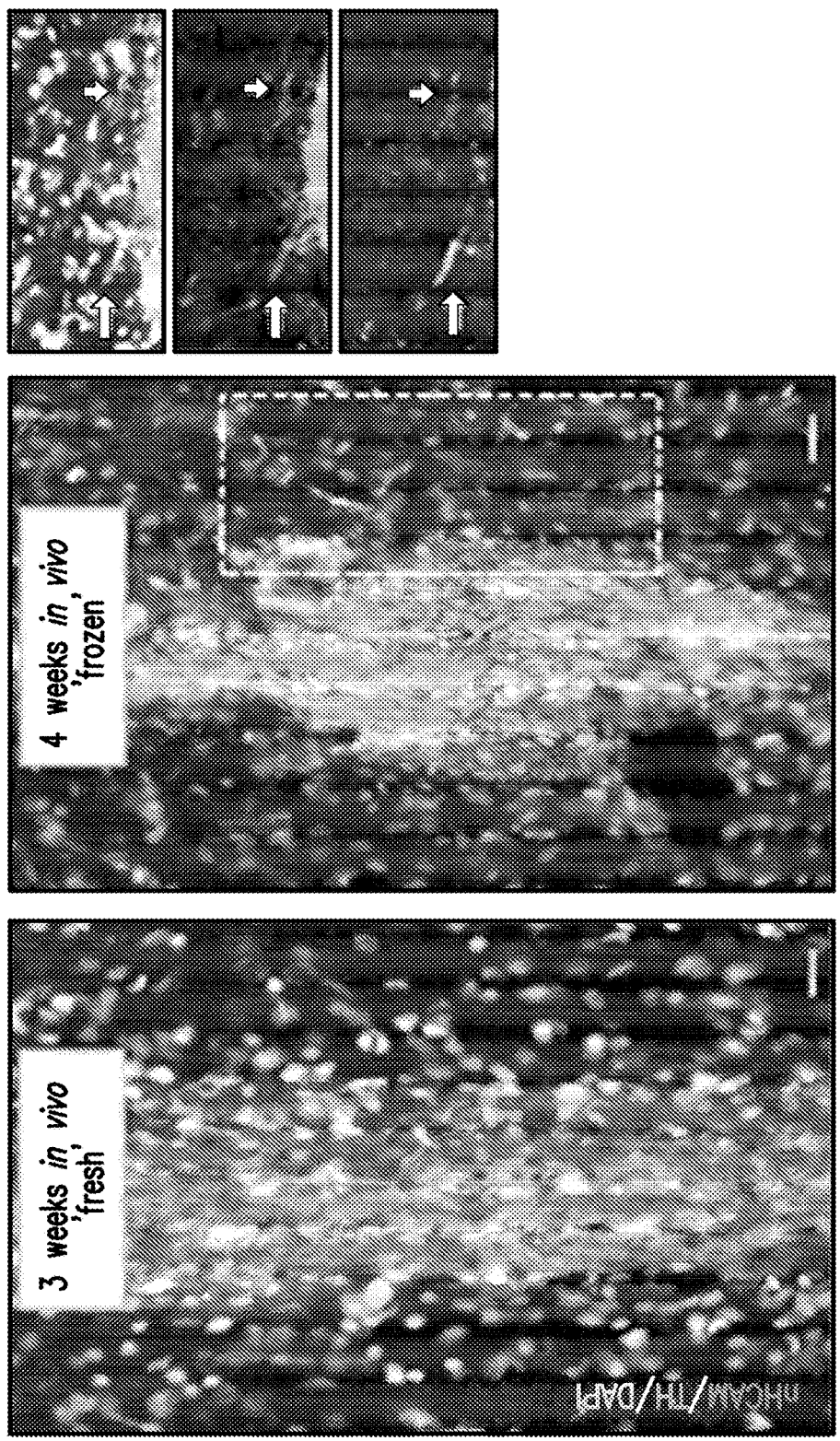

FIG. 8 shows that cryopreserved midbrain DA neurons behave similarly in vivo when compared to 'fresh' cells. Expression of Hncam and TH in 3-week grafts of "fresh" and 4-week grafts of "frozen" cells transplanted into mice was compared. Both grafts showed early signs of fiber outgrowth as highlighted in the insert panels on the right.

Figure 9A:
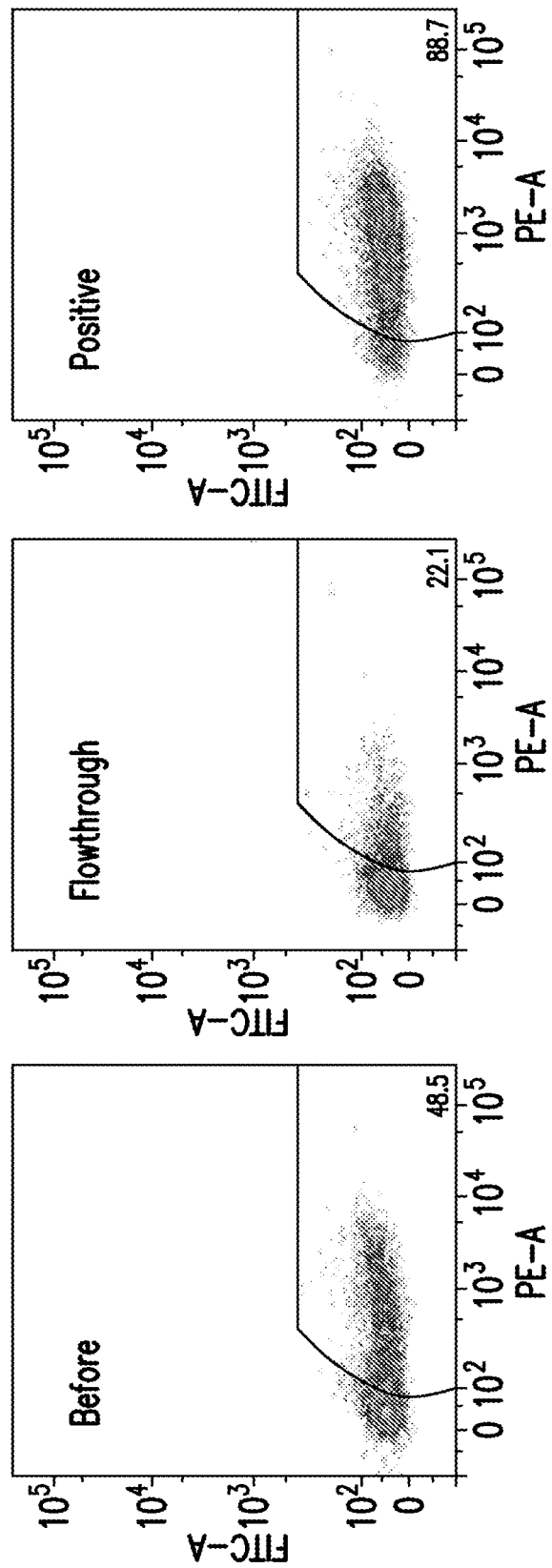
Figure 9B:
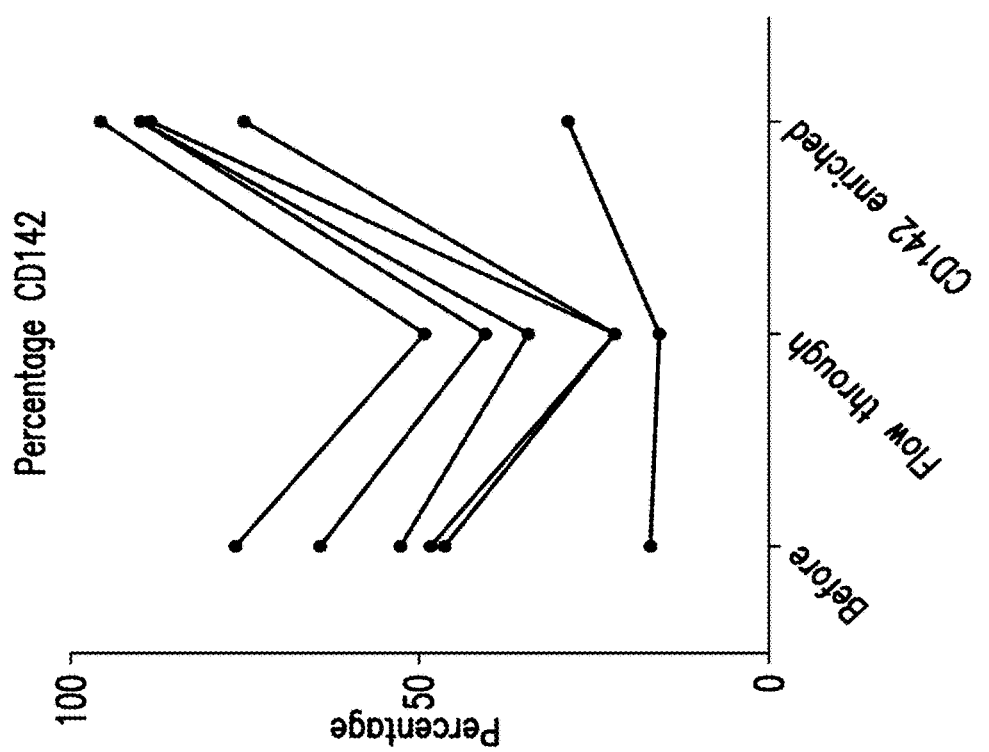

FIG. 9A-B shows (A) cell sorting of midbrain DA cells expressing CD142 using MACS flow cytometry. The presort ("before"), flow through (negative fraction) and positive fraction of Day 24, CD142 sorted mDA neurons are shown. Phycoerythrin was conjugated to CD142 and anti-PE beads were used for isolation to visualize the results. (B) Shows the consistency across 6 experiments.

Figure 10A:
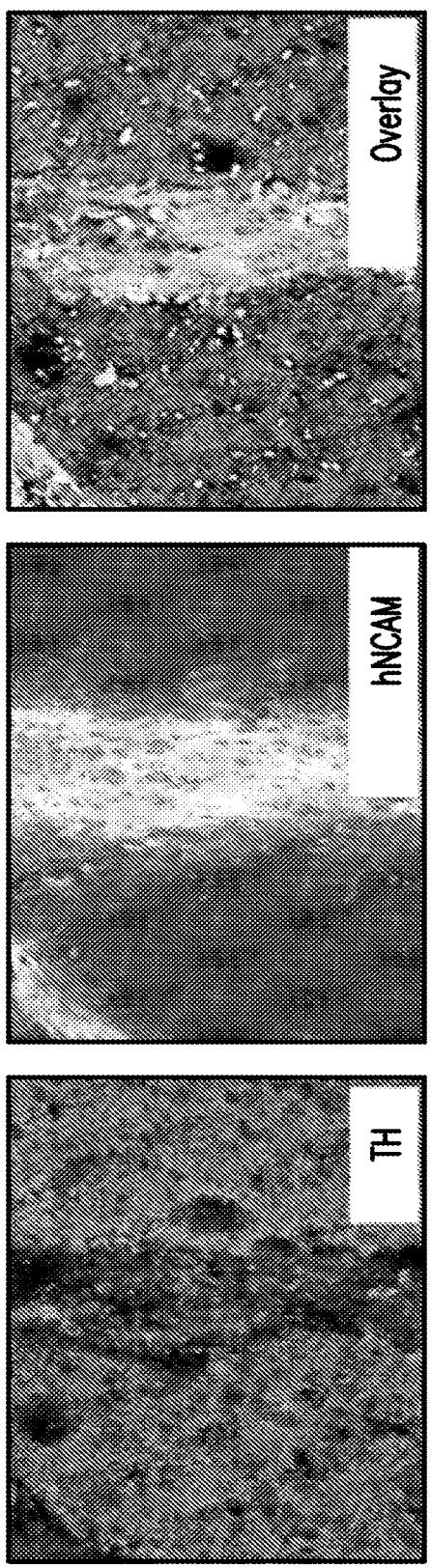
Figure 10B:
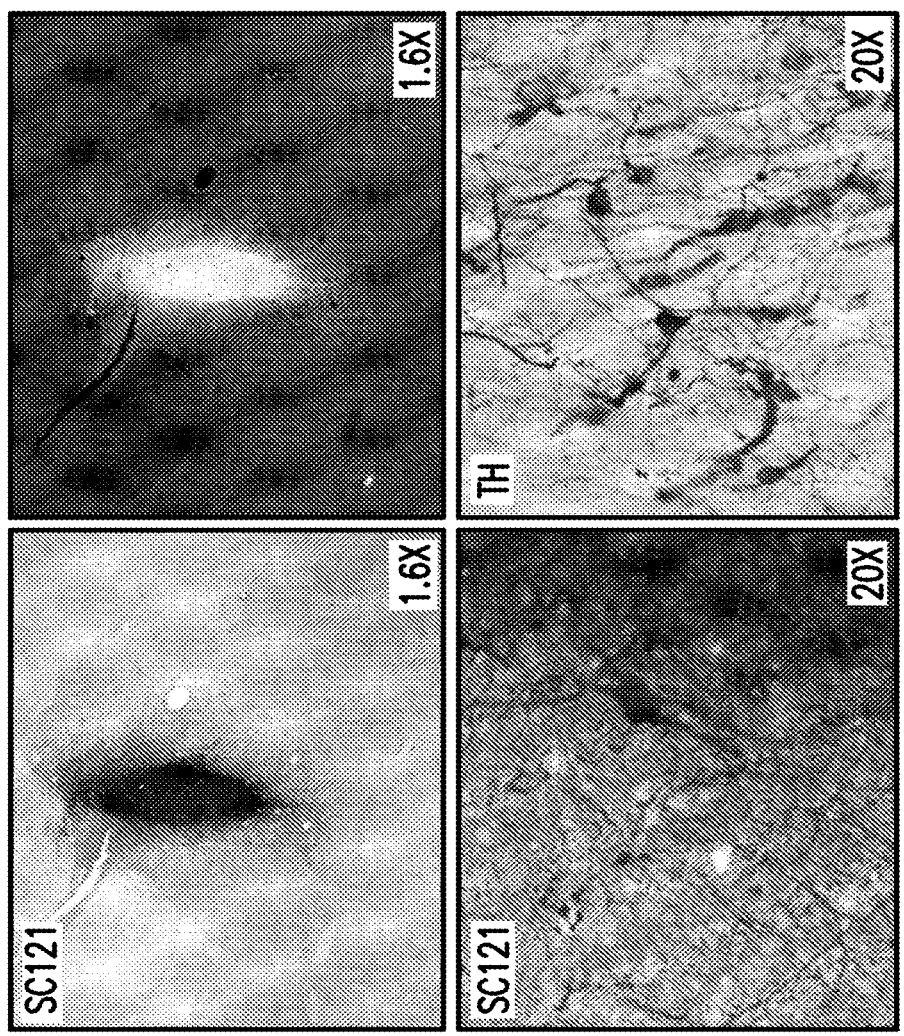

FIG. 10A-B shows that mDA neurons survive in unlesioned mice and Parkinsonian monkeys. (A) CD142 sorted mA cells survive in vivo. mDA neurons prepared in KSR according to the method described by Kirks et al. were sorted by FACS for CD142 and transplanted into mice. Grafts were harvested 30 days after transplantation and analyzed for the expression of TH and hNCAM. (B) KSR protocol-derived (Kriks et al.) mDA neurons survive 1 year in non-human primates (NHPs). Day 25 mDA neurons were grafted into Parkinsonian monkeys, and grafts were collected 12 months post-grafting. Sections were stained with antibodies detecting human cytoplasm (SC121) and TH. Upper half shows the regular and inverted images, while the lower half shows higher power magnifications. Data indicate that MACS sorted cells showed comparable survival to CD142 sorted mDA cells grafted into mice.

FIG. 11A-D shows the effect of polysialyltransferase treatment (*Neisseria meningitidis* polysialyltransferase ($PST_{Nm}$)) of mDA neurons in vitro. (A) Shows the effects of cryopreservation on polysialylation (PSA) levels. mDA cells were either treated with $PST_{Nm}$ or left without modification. Half the cells were fixed while the other half was cryopreserved. Frozen cells were thawed 1 week later and also fixed. Cells were immunostained for PSA and analyzed by flow cytometry. Black lines indicate fresh, unstained cells. Staining of PSTNm—induced PSA is identical in frozen and unfrozen cells. Blue line represents untreated cells analyzed fresh, and the red and green line are from PSTNm treated cells either analyzed fresh (red), or after cryo storage (green). (B) Shows the effects of PSTNm treatment on CD142 cell sorted cells. Representative images of TAU-1 staining after 1 day in culture of CD142 sorted cells that were either untreated (left), or PSTNm treated (right). (C) Shows that PSTNm—treated, CD142 sorted cells, exhibited enhanced axonal length. Cells were analyzed at Day 1 or Day 4 and images quantified using NIH's ImageJ software. (D) Shows that PSA levels persist in vivo. PSTNm treated mDA neurons were transplanted in the striatum of mice, and PSA levels were visualized 2 weeks after grafting. Two fields of view (FOV 1 and FOV 2) are shown per condition. The right graph summarizes the results.

Figure 12:
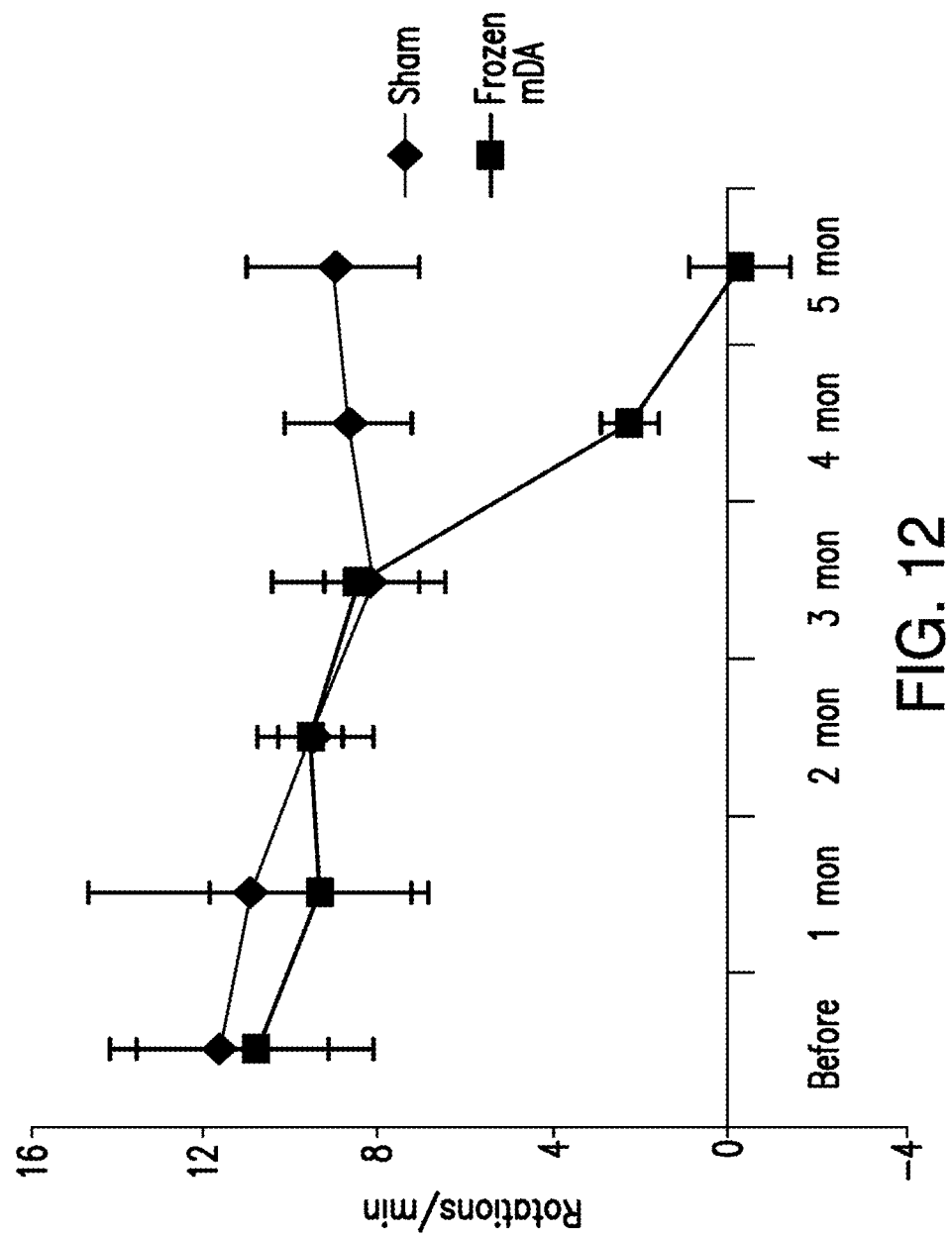

FIG. 12 shows the rotational behavior of lesioned rats transplanted with mDA precursors differentiated as described by Example 2 and cryopreserved at day 16, compared to sham transplanted rats. Rats were tested before transplantation, and at 1, 2, 3, 4 and 5 months after transplantation. Rotational behavior was induced by amphetamine administration. Lesioned rats that received transplants exhibited a statistically significant reduction in rotational behavior compared to sham transplanted rats at four months post-transplantation.

Figure 13:
Figure 13:
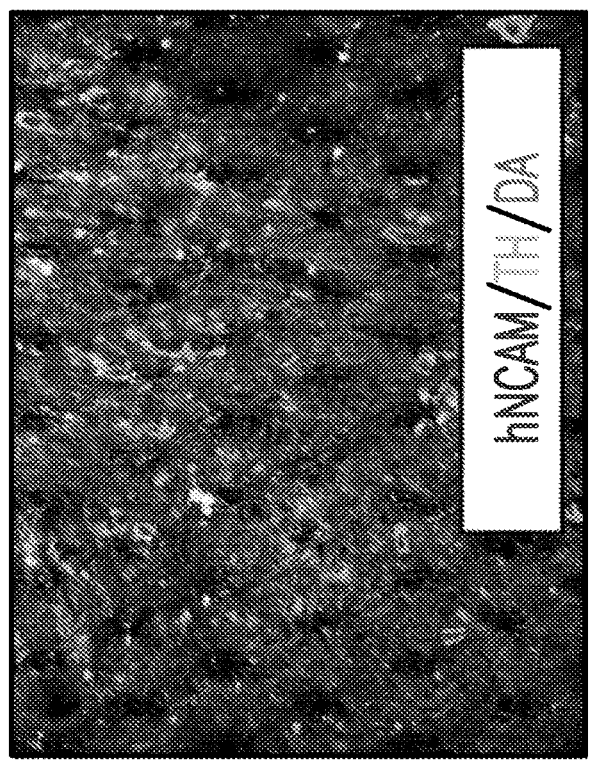

FIG. 13 shows the in vivo expression of hNCAM, TH, and GIRK2 in lesioned rats transplanted with mDA precursors differentiated as described by Example 2 and cryopreserved at day 16. Transplanted grafts were examined five months post-transplantation. TH staining showed typical mDA morphology. TH positive neurons were also GIRK2 positive.

Figure 14:
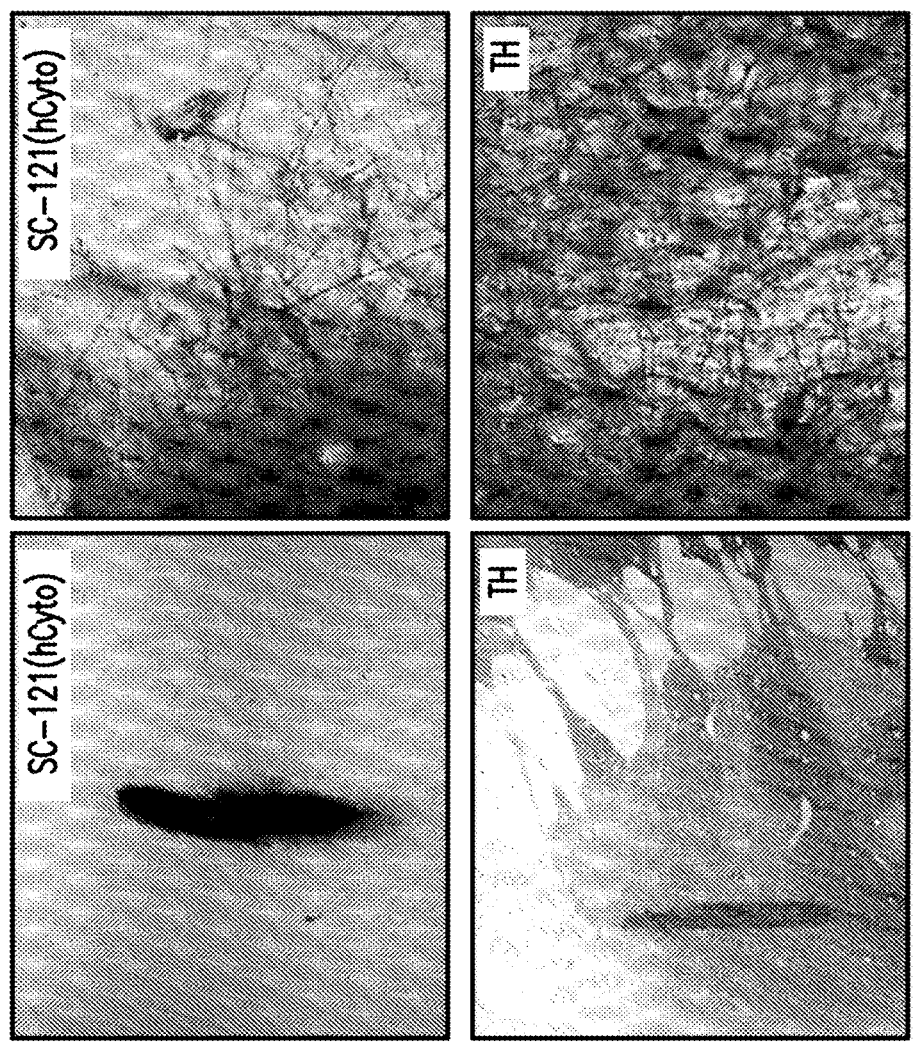

FIG. 14 shows that mDA precursors differentiated according to Example 2, and cryopreserved at day 16, survived for 6 weeks following thawing and transplantation into non-human primates. The transplanted grafts exhibited robust fiber outgrowth from the graft core and also exhibited typical mDA morphology.

5. DETAILED DESCRIPTION OF THE INVENTION

The presently disclosed subject matter relates to methods for inducing differentiation of human stem cells to cells that express one or more markers of midbrain dopamine (mDA) cells or precursors thereof, compositions of cells expressing such markers, and methods for treating neurodegenerative disorders.

For purposes of clarity of disclosure and not by way of limitation, the detailed description is divided into the following subsections:

5.1. Definitions;
5.2. Method of Differentiating Stem Cells;
5.3. Method of Treating Neurodegenerative disorders; and
5.4. Kits.

5.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold, or within 2-fold, of a value.

As used herein, the term "signaling" in reference to a "signal transduction protein" refers to a protein that is activated or otherwise affected by ligand binding to a membrane receptor protein or some other stimulus. Examples of signal transduction protein include, but are not limited to, a SMAD, a wingless (Wnt) complex protein, including beta-catenin, NOTCH, transforming growth factor beta (TGFβ), Activin, Nodal, glycogen synthase kinase 3β (GSK3 β) proteins, bone morphogenetic proteins (BMP) and fibroblast growth factors (FGF). For many cell surface receptors or internal receptor proteins, ligand-receptor interactions are not directly linked to the cell's response. The ligand activated receptor can first interact with other proteins inside the cell before the ultimate physiological effect of the ligand on the cell's behavior is produced. Often, the behavior of a chain of several interacting cell proteins is altered following receptor activation or inhibition. The entire set of cell changes induced by receptor activation is called a signal transduction mechanism or signaling pathway.

As used herein, the term "signals" refer to internal and external factors that control changes in cell structure and function. They can be chemical or physical in nature.

As used herein, the term "ligands" refers to molecules and proteins that bind to receptors, e.g., transforming growth factor-beta (TFGβ), Activin, Nodal, bone morphogenic proteins (BMPs), etc.

"Inhibitor" as used herein, refers to a compound or molecule (e.g., small molecule, peptide, peptidomimetic, natural compound, siRNA, anti-sense nucleic acid, aptamer, or antibody) that interferes with (e.g., reduces, decreases, suppresses, eliminates, or blocks) the signaling function of the molecule or pathway. An inhibitor can be any compound or molecule that changes any activity of a named protein (signaling molecule, any molecule involved with the named signaling molecule, a named associated molecule, such as a glycogen synthase kinase 3β (GSK3β)) (e.g., including, but not limited to, the signaling molecules described herein), for one example, via directly contacting SMAD signaling, contacting SMAD mRNA, causing conformational changes of SMAD, decreasing SMAD protein levels, or interfering with SMAD interactions with signaling partners (e.g., including those described herein), and affecting the expression of SMAD target genes (e.g. those described herein). Inhibitors also include molecules that indirectly regulate biological activity, for example, SMAD biological activity, by intercepting upstream signaling molecules (e.g., within the extracellular domain, examples of a signaling molecule and an effect include: Noggin which sequesters bone morphogenic proteins, inhibiting activation of ALK receptors 1,2,3, and 6, thus preventing downstream SMAD activation. Likewise, Chordin, Cerberus, Follistatin, similarly sequester extracellular activators of SMAD signaling. Bambi, a transmembrane protein, also acts as a pseudo-receptor to sequester extracellular TGFb signaling molecules). Antibodies that block upstream or downstream proteins are contemplated for use to neutralize extracellular activators of protein signaling, and the like. Inhibitors are described in terms of competitive inhibition (binds to the active site in a manner as to exclude or reduce the binding of another known binding compound) and allosteric inhibition (binds to a protein in a manner to change the protein conformation in a manner which interferes with binding of a compound to that protein's active site) in addition to inhibition induced by binding to and affecting a molecule upstream from the named signaling molecule that in turn causes inhibition of the named molecule. An inhibitor can be a "direct inhibitor" that inhibits a signaling target or a signaling target pathway by actually contacting the signaling target.

"Activators," as used herein, refer to compounds that increase, induce, stimulate, activate, facilitate, or enhance activation the signaling function of the molecule or pathway, e.g., Wnt signaling, SHH signaling, etc.

As used herein, the term "derivative" refers to a chemical compound with a similar core structure.

As used herein, the term "a population of cells" or "a cell population" refers to a group of at least two cells. In non-limiting examples, a cell population can include at least about 10, at least about 100, at least about 200, at least about 300, at least about 400, at least about 500, at least about 600, at least about 700, at least about 800, at least about 900, at least about 1000 cells. The population may be a pure population comprising one cell type, such as a population of midbrain DA precursors, or a population of undifferentiated stem cells. Alternatively, the population may comprise more than one cell type, for example a mixed cell population.

As used herein, the term "stem cell" refers to a cell with the ability to divide for indefinite periods in culture and to give rise to specialized cells.

As used herein, the term "embryonic stem cell" and "ESC" refer to a primitive (undifferentiated) cell that is derived from preimplantation-stage embryo, capable of dividing without differentiating for a prolonged period in culture, and are known to develop into cells and tissues of the three primary germ layers. A human embryonic stem cell refers to an embryonic stem cell that is from a human embryo. As used herein, the term "human embryonic stem cell" or "hESC" refers to a type of pluripotent stem cells derived from early stage human embryos, up to and including the blastocyst stage, that is capable of dividing without differentiating for a prolonged period in culture, and are known to develop into cells and tissues of the three primary germ layers.

As used herein, the term "embryonic stem cell line" refers to a population of embryonic stem cells which have been cultured under in vitro conditions that allow proliferation without differentiation for up to days, months to years.

As used herein, the term "totipotent" refers to an ability to give rise to all the cell types of the body plus all of the cell types that make up the extraembryonic tissues such as the placenta.

As used herein, the term "multipotent" refers to an ability to develop into more than one cell type of the body.

As used herein, the term "pluripotent" refers to an ability to develop into the three developmental germ layers of the organism including endoderm, mesoderm, and ectoderm.

As used herein, the term "induced pluripotent stem cell" or "iPSC" refers to a type of pluripotent stem cell formed by the introduction of certain embryonic genes (such as but not limited to OCT4, SOX2, and KLF4 transgenes) (see, for example, Takahashi and Yamanaka Cell 126, 663-676 (2006), herein incorporated by reference) into a somatic cell.

As used herein, the term "somatic cell" refers to any cell in the body other than gametes (egg or sperm); sometimes referred to as "adult" cells.

As used herein, the term "somatic (adult) stem cell" refers to a relatively rare undifferentiated cell found in many organs and differentiated tissues with a limited capacity for both self renewal (in the laboratory) and differentiation.

As used herein, the term "neuron" refers to a nerve cell, the principal functional units of the nervous system. A neuron consists of a cell body and its processes—an axon and one or more dendrites. Neurons transmit information to other neurons or cells by releasing neurotransmitters at synapses.

As used herein, the term "proliferation" refers to an increase in cell number.

As used herein, the term "undifferentiated" refers to a cell that has not yet developed into a specialized cell type.

As used herein, the term "differentiation" refers to a process whereby an unspecialized embryonic cell acquires the features of a specialized cell such as a neuron, heart, liver, or muscle cell. Differentiation is controlled by the interaction of a cell's genes with the physical and chemical conditions outside the cell, usually through signaling pathways involving proteins embedded in the cell surface.

As used herein, the term "directed differentiation" refers to a manipulation of stem cell culture conditions to induce differentiation into a particular (for example, desired) cell type, such as neural, neural crest, cranial placode, and non-neural ectoderm precursors.

As used herein, the term "directed differentiation" in reference to a stem cell refers to the use of small molecules, growth factor proteins, and other growth conditions to promote the transition of a stem cell from the pluripotent state into a more mature or specialized cell fate.

As used herein, the term "inducing differentiation" in reference to a cell refers to changing the default cell type (genotype and/or phenotype) to a non-default cell type (genotype and/or phenotype). Thus, "inducing differentiation in a stem cell" refers to inducing the stem cell (e.g., human stem cell) to divide into progeny cells with characteristics that are different from the stem cell, such as genotype (e.g., change in gene expression as determined by genetic analysis such as a microarray) and/or phenotype (e.g., change in expression of a protein marker of midbrain DA cells, or precursors thereof, such as EN-1, OTX2, TH, NURR1, FOXA2, and LLMX1A).

As used herein, the term "cell culture" refers to a growth of cells in vitro in an artificial medium for research or medical treatment.

As used herein, the term "culture medium" refers to a liquid that covers cells in a culture vessel, such as a Petri plate, a multi-well plate, and the like, and contains nutrients to nourish and support the cells. Culture medium may also include growth factors added to produce desired changes in the cells.

As used herein, the term "contacting" a cell or cells with a compound (e.g., one or more inhibitor, activator, and/or inducer) refers to providing the compound in a location that permits the cell or cells access to the compound. The contacting may be accomplished using any suitable method. For example, contacting can be accomplished by adding the compound, in concentrated form, to a cell or population of cells, for example in the context of a cell culture, to achieve the desired concentration. Contacting may also be accomplished by including the compound as a component of a formulated culture medium.

As used herein, the term "in vitro" refers to an artificial environment and to processes or reactions that occur within an artificial environment. In vitro environments exemplified, but are not limited to, test tubes and cell cultures.

As used herein, the term "in vivo" refers to the natural environment (e.g., an animal or a cell) and to processes or reactions that occur within a natural environment, such as embryonic development, cell differentiation, neural tube formation, etc.

As used herein, the term "expressing" in relation to a gene or protein refers to making an mRNA or protein which can be observed using assays such as microarray assays, antibody staining assays, and the like.

As used herein, the term "marker" or "cell marker" refers to gene or protein that identifies a particular cell or cell type. A marker for a cell may not be limited to one marker, markers may refer to a "pattern" of markers such that a designated group of markers may identity a cell or cell type from another cell or cell type.

As used herein, the term "derived from" or "established from" or "differentiated from" when made in reference to any cell disclosed herein refers to a cell that was obtained from (e.g., isolated, purified, etc.) an ultimate parent cell in a cell line, tissue (such as a dissociated embryo, or fluids using any manipulation, such as, without limitation, single cell isolation, culture in vitro, treatment and/or mutagenesis using for example proteins, chemicals, radiation, infection with virus, transfection with DNA sequences, such as with a morphogen, etc., selection (such as by serial culture) of any cell that is contained in cultured parent cells. A derived cell can be selected from a mixed population by virtue of response to a growth factor, cytokine, selected progression of cytokine treatments, adhesiveness, lack of adhesiveness, sorting procedure, and the like.

An "individual" or "subject" herein is a vertebrate, such as a human or non-human animal, for example, a mammal. Mammals include, but are not limited to, humans, non-human primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

5.2 Method of Differentiating Stem Cells

The presently disclosed subject matter is based at least in part on the discovery that midbrain dopamine (mDA) neurons, and precursors thereof, can be differentiated from human stem cells by dual inhibition of SMAD signaling (for example, by inhibition of TGFβ/Activin-Nodal signaling and BMP signaling), along with the activation of Sonic Hedgehog (SHH) signaling, and activation of wingless (Wnt) signaling, wherein the concentration of a Wnt activating compound is increased about 4 days after initial contact of the cells to the SMAD inhibitors, SHH activator, and Wnt activator. In certain non-limiting embodiments, said increase in the concentration of Wnt activating compound may be about 400% to 1000% of the concentration of Wnt activating compound prior to said increase. In certain non-limiting embodiments, said higher concentration of Wnt activator may be maintained for at least about 7 or 8 days. In certain non-limiting embodiments, the increase in Wnt activation is achieved by adding a second or more Wnt activator. The cells can be further contacted with midbrain DA lineage specific activators and inhibitors, for example, BDNF, GDNF, cAMP, TGFβ, AA, and DAPT. In certain non-limiting embodiments, an effective amount of increased Wnt activator concentration is that concentration which reduces the detectable level of PAX6 expression in a population of cells contacted with the Wnt activator. In certain non-limiting embodiments, PAX6 expression is not detectable in the population of cells.

The presently disclosed subject matter provides for in vitro methods for inducing differentiation of stem cells (e.g., human stem cells). Non-limiting examples of human stem cells include human embryonic stem cells (hESC), human pluripotent stem cells (hPSC), human induced pluripotent stem cells (hiPSC), human parthenogenetic stem cells, primordial germ cell-like pluripotent stem cells, epiblast stem cells, F-class pluripotent stem cells, somatic stem cells, cancer stem cells, or any other cell capable of lineage specific differentiation. In certain embodiments, the human stem cell is a human embryonic stem cell (hESC). In certain embodiments, the human stem cell is a human induced pluripotent stem cell (hiPSC).

Non-limiting examples of stem cells that can be used in accordance with the methods described by the present application also include human, nonhuman primate or rodent nonembryonic stem cells, embryonic stem cells, induced nonembryonic pluripotent cells and engineered pluripotent cells.

In certain non-limiting embodiments, the stem cell or a progeny cell thereof contains an introduced heterologous nucleic acid, where said nucleic acid may encode a desired nucleic acid or protein product or have informational value (see, for example, U.S. Pat. No. 6,312,911, which is incorporated by reference in its entirety). Non-limiting examples of desired protein products include markers detectable via in vivo imaging studies, for example receptors or other cell membrane proteins such as but not limited to the human sodium iodine symporter.

Non-limiting examples of markers further include fluorescent proteins (such as green fluorescent protein (GFP), blue fluorescent protein (EBFP, EBFP2, Azurite, mKalama1), cyan fluorescent protein (ECFP, Cerulean, CyPet, mTurquoise2), and yellow fluorescent protein derivatives (YFP, Citrine, Venus, YPet, EYFP)), β-galactosidase (LacZ), chloramphenicol acetyltransferase (cat), neomycin phosphotransferase (neo), enzymes (such as oxidases and peroxidases), and antigenic molecules. As used herein, the terms "reporter gene" or "reporter construct" refer to genetic constructs comprising a nucleic acid encoding a protein that is easily detectable or easily assayable, such as a colored protein, fluorescent protein such as GFP or an enzyme such as beta-galactosidase (lacZ gene). In certain embodiments, the reporter can be driven by a recombinant promoter of an mDA marker gene, for example, TH and/or En-1.

In certain non-limiting embodiments, the stem cell, or a progeny cell thereof, contains an introduced heterologous nucleic acid that increases or decreases the metabolic processes of the cell, for example, glucose metabolism and/or choline metabolism, wherein the cell can be imaged in vivo using Positron Emission Tomography (PET) due to the altered metabolic activity.

In certain embodiments, a presently disclosed differentiation method comprises contacting a population of human stem cells with one or more inhibitor of transforming growth factor beta (TGFβ/Activin-Nodal signaling, which results in inhibition of Small Mothers Against Decapentaplegic (SMAD) signaling. In certain embodiments, the inhibitor of TGFβ/Activin-Nodal signaling neutralizes the ligands including TGFβs, bone morphogenetic proteins (BMPs), Nodal, and activins, or blocking their signal pathways through blocking the receptors and downstream effectors. Non-limiting examples of inhibitors of TGFβ/Activin-Nodal signaling are disclosed in WO/2010/096496, WO/2011/149762, WO/2013/067362, WO/2014/176606, WO/2015/077648, Chambers et al., Nat Biotechnol. 2009 March; 27(3):275-80, Kriks et al., Nature. 2011 Nov. 6; 480(7378): 547-51, and Chambers et al., Nat Biotechnol. 2012 Jul. 1; 30(7):715-20 (2012), which are incorporated by reference in their entireties herein for all purposes. In certain embodiments, the one or more inhibitor of TGFβ/Activin-Nodal signaling is a small molecule selected from the group consisting of SB431542, derivatives thereof, and mixtures thereof. "SB431542" refers to a molecule with a number CAS 301836-41-9, a molecular formula of $C_{22}H_{18}N_4O_3$, and a name of 4-[4-(1,3-benzodioxol-5-yl)-5-(2-pyridinyl)-1H-imidazol-2-yl]-benzamide, for example, see structure below:

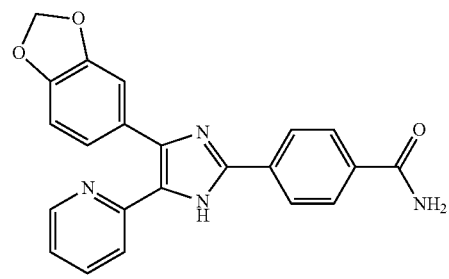

A presently disclosed differentiation method further comprises contacting the human stem cells with one or more inhibitor of BMP signaling, which results in inhibition of SMAD signaling. Non-limiting examples of inhibitors of SMAD signaling are disclosed in WO2011/149762, Chambers et al., Nat Biotechnol. 2009 March; 27(3):275-80, Kriks et al., Nature. 2011 Nov. 6; 480(7378):547-51, and Chambers et al., Nat Biotechnol. 2012 Jul. 1; 30(7):715-20, which are incorporated by reference in their entireties. In certain embodiments, the one or more inhibitor of BMP/SMAD signaling is a small molecule selected from the group consisting of LDN193189, derivatives thereof, and mixtures thereof "LDN193189" refers to a small molecule DM-3189, IUPAC name 4-(6-(4-(piperazin-1-yl)phenyl)pyrazolo[1,5-a]pyrimidin-3-yl)quinoline, with a chemical formula of $C_{25}H_{22}N_6$ with the following formula.

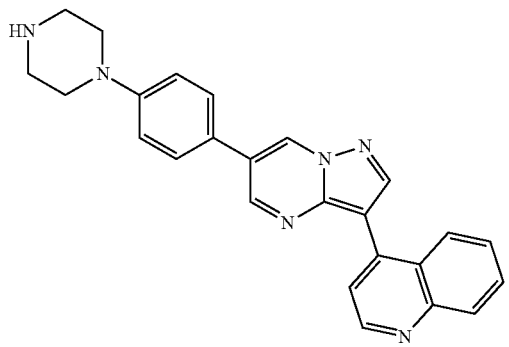 [SMILES: c1ccc2c(-c3cnn4cc(-c5ccc(N6CCNCC6)cc5)cnc34)ccnc2c1]

LDN193189 is capable of functioning as a SMAD signaling inhibitor. LDN193189 is also highly potent small-molecule inhibitor of ALK2, ALK3, and ALK6, protein tyrosine kinases (PTK), inhibiting signaling of members of the ALK1 and ALK3 families of type I TGFβ receptors, resulting in the inhibition of the transmission of multiple biological signals, including the bone morphogenetic proteins (BMP) BMP2, BMP4, BMP6, BMP7, and Activin cytokine signals and subsequently SMAD phosphorylation of Smad1, Smad5, and Smad8 (Yu et al. (2008) Nat Med 14:1363-1369; Cuny et al. (2008) Bioorg. Med. Chem. Lett. 18: 4388-4392, herein incorporated by reference).

A presently disclosed differentiation method further comprises contacting the human stem cells with one or more activator of Wnt signaling. As used herein, the term "WNT" or "wingless" in reference to a ligand refers to a group of secreted proteins (i.e. Intl (integration 1) in humans) capable of interacting with a WNT receptor, such as a receptor in the Frizzled and LRPDerailed/RYK receptor family. As used herein, the term "WNT" or "wingless" in reference to a signaling pathway refers to a signal pathway composed of Wnt family ligands and Wnt family receptors, such as Frizzled and LRPDerailed/RYK receptors, mediated with or without β-catenin. For the purposes described herein, a preferred WNT signaling pathway includes mediation by β-catenin, e.g., WNT/-catenin.

In certain embodiments, the one or more activator of Wnt signaling lowers GSK3β for activation of Wnt signaling. Thus, the activator of Wnt signaling can be a GSK3β inhibitor. A GSK3P inhibitor is capable of activating a WNT signaling pathway, see e.g., Cadigan, et al., J Cell Sci. 2006; 119:395-402; Kikuchi, et al., Cell Signaling. 2007; 19:659-671, which are incorporated by reference herein in their entireties. As used herein, the term "glycogen synthase kinase 3β inhibitor" refers to a compound that inhibits a glycogen synthase kinase 3β enzyme, for example, see, Doble, et al., J Cell Sci. 2003; 116:1175-1186, which is incorporated by reference herein in its entirety.

Non-limiting examples of activators of Wnt signaling or GSK3P inhibitors are disclosed in WO2011/149762, WO13/067362, Chambers et al., Nat Biotechnol. 2012 Jul. 1; 30(7):715-20, Kriks et al., Nature. 2011 Nov. 6; 480(7378): 547-51, and Calder et al., J Neurosci. 2015 Aug. 19; 35(33): 11462-81, which are incorporated by reference in their entireties. In certain embodiments, the one or more activator of Wnt signaling is a small molecule selected from the group consisting of CHIR99021, derivatives thereof, and mixtures thereof. "CHIR99021" (also known as "aminopyrimidine" or "3-[3-(2-Carboxyethyl)-4-methylpyrrol-2-methylidenyl]-2-indolinone") refers to IUPAC name 6-(2-(4-(2,4-dichlorophenyl)-5-(4-methyl-1H-imidazol-2-yl)pyrimidin-2-ylamino) ethylamino)nicotinonitrile with the following formula.

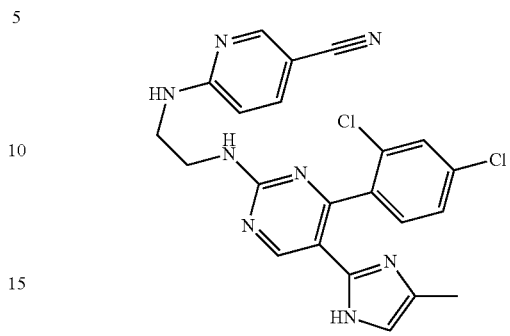

CHIR99021 is highly selective, showing nearly thousand-fold selectivity against a panel of related and unrelated kinases, with an IC50=6.7 nM against human GSK3P and nanomolar IC50 values against rodent GSK3β homologs.

In certain non-limiting embodiments, the population of cells described herein are contacted with and initial concentration of CHIR99021 at a concentration of between about 0.001 and 2 μM, or between about 0.01 and 1.5 μM, or between about 0.1 and 1 μM, or between about 0.5 and 0.8 μM, or about 0.7 μM, wherein the concentration of CHIR99021 is increased, as described herein, for example, about 4 days after initial contact of the cells to CHIR99021, to between about 2 and 15 μM, or between abut 3 and 14 μM, or between about 4 and 13 μM, or between about 5 and 12 μM, or between about 6 and 11 μM, or between about 7 and 10 μM, or between about 8 and 9 μM, or between about 3 and 10 μM, or between about 5 and 10 μM, or about 3 μM, or about 7.5 μM.

A presently disclosed differentiation method further comprises contacting the human stem cells with one or more activator of SHH signaling. As used herein, the term "Sonic hedgehog," "SHH," or "Shh" refers to a protein that is one of at least three proteins in the mammalian signaling pathway family called hedgehog, another is desert hedgehog (DHH) while a third is Indian hedgehog (IHH). Shh interacts with at least two transmembrane proteins by interacting with transmembrane molecules Patched (PTC) and Smoothened (SMO). Shh typically binds to PTC which then allows the activation of SMO as a signal transducer. In the absence of SHH, PTC typically inhibits SMO, which in turn activates a transcriptional repressor so transcription of certain genes does not occur. When Shh is present and binds to PTC, PTC cannot interfere with the functioning of SMO. With SMO uninhibited, certain proteins are able to enter the nucleus and act as transcription factors allowing certain genes to be activated (see, Gilbert, 2000 Developmental Biology (Sunderland, Mass., Sinauer Associates, Inc., Publishers). In certain embodiments, an activator of Sonic hedgehog (SHH) signaling refers to any molecule or compound that activates a SHH signaling pathway, including a molecule or compound that binds to PTC or a Smoothened agonist and the like. Non-limiting examples of activators of Wnt signaling or GSK3P inhibitors are disclosed in WO10/096496, WO13/067362, Chambers et al., Nat Biotechnol. 2009 March; 27(3):275-80, and Kriks et al., Nature. 2011 Nov. 6; 480 (7378):547-51. Examples of such compounds are recombinant SHH, purified SHH, a protein Sonic hedgehog (SHH) C25II (i.e., a recombinant N-Terminal fragment of a full-length murine sonic hedgehog protein capable of binding to the SHH receptor for activating SHH, for example, R and D Systems catalog number: 464-5H-025/CF) and a small molecule Smoothened agonist such as, for example, purmorphamine.

In certain embodiments, the above-described inhibitors and activators are added to a cell culture medium comprising the stem cells. Suitable cell culture media include, but are not limited to, Knockout® Serum Replacement ("KSR") medium, Neurobasal® medium (NB), N2 medium, B-27 medium, and Essential 8®/Essential 6® ("E8/E6") medium, and combinations thereof. KSR medium, NB medium, N2 medium, B-27 medium, and E8/E6 medium are commercially available. KSR medium is a defined, serum-free formulation optimized to grow and maintain undifferentiated hESC cells in culture.

In certain embodiments, the cell culture medium is a KSR medium. The components of a KSR medium are disclosed in WO2011/149762. In certain embodiments, a KSR medium comprises Knockout DMEM, Knockout Serum Replacement, L-Glutamine, Pen/Strep, MEM, and 13-mercaptoethanol. In certain embodiments, 1 liter of KSR medium comprises 820 mL of Knockout DMEM, 150 mL of Knockout Serum Replacement, 10 mL of 200 mM L-Glutamine, 10 mL of Pen/Strep, 10 mL of 10 mM MEM, and 55 µM of 13-mercaptoethanol.

In certain embodiments, the stem cells are contacted with one or more inhibitor of TGFβ/Activin-Nodal signaling, one or more inhibitor of BMP/SMAD signaling, one or more activator of Wnt signaling, and one or more activator of SHH signaling. In certain embodiments, one or more inhibitor of TGFβ/Activin-Nodal signaling, one or more inhibitor of SMAD signaling, one or more activator of Wnt signaling, and one or more activator of SHH signaling are added to a cell culture medium comprising the stem cells.

In certain embodiments, the cell culture medium is an E8/E6 medium. E8/E6 medium is a feeder-free and xeno-free medium that supports the growth and expansion of human pluripotent stem cells. E8/E6 medium has been proven to support somatic cell reprogramming. In addition, E8/E6 medium can be used as a base for the formulation of custom media for the culture of PSCs. One example E8/E6 medium is described in Chen et al., Nat Methods 2011 May; 8(5):424-9, which is incorporated by reference in its entirety. One example E8/E6 medium is disclosed in WO15/077648, which is incorporated by reference in its entirety. In certain embodiments, an E8/E6 cell culture medium comprises DMEM/F12, ascorbic acid, selenium, insulin, NaHCO$_3$, transferrin, FGF2 and TGFβ. The E8/E6 medium differs from a KSR medium in that E8/E6 medium does not include an active BMP or Wnt ingredient. Thus, in certain embodiments, when an E8/E6 medium is used to culture the presently disclosed population of stem cells to differentiate into a population of proprioceptors, one or more inhibitor of SMAD signaling (e.g., those inhibiting BMP) is not required to be added to the E8/E6 medium. In certain embodiments, the stem cells are contacted with one or more inhibitor of TGFβ/Activin-Nodal signaling, one or more activator of Wnt signaling, and one or more activator of SHH signaling. In certain embodiments, the stem cells are contacted with one or more inhibitor of TGFβ/Activin-Nodal signaling, one or more activator of Wnt signaling, and one or more activator of SHH signaling are added to a cell culture medium comprising the stem cells. In certain embodiments, BMP can be further added to the medium.

In certain embodiments, the presently disclosed subject matter provides for in vitro methods for inducing differentiation of human stem cells into midbrain DA neurons, or precursors thereof. In certain embodiments, the stem cells are contacted with one or more inhibitor of TGFβ/Activin-Nodal signaling, one or more inhibitor of BMP/SMAD signaling, one or more activator of Wnt signaling, and one or more activator of SHH signaling concurrently, e.g., by adding these inhibitors to a cell culture medium comprising the stem cells on the same day. In certain embodiments, the concentration of the one or more activator of Wnt signaling is increased at least about 2, 3, 4, 5 or 6 days after the cells are initially contacted with the Wnt activator.

In certain embodiments, the one or more inhibitor of TGFβ/Activin-Nodal signaling is contacted to the cells for at least about 4, 5, 6, 7, 8, 9, or 10 or more days, for example, between about 4 and 10 days, or between about 5 and 9 days, or between about 6 and 8 days. In certain embodiments, the one or more inhibitor of TGFβ/Activin-Nodal signaling is contacted to the cells for up to about 4, 5, 6, 7, 8, 9, or 10 or more days. In certain embodiments, the one or more inhibitor of TGFβ/Activin-Nodal signaling is contacted to the cells for about 7 days. In certain embodiments, the one or more inhibitor of TGFβ/Activin-Nodal signaling is added every day or every other day to a cell culture medium comprising the stem cells from day 0 to day 10 (e.g., added on day 0, day 2, day 4, day 6, day 8, and day 10). In certain embodiments, the one or more inhibitor of TGFβ/Activin-Nodal signaling is added on days 0, 1, 3, 4, and 6.

In certain embodiments, the one or more inhibitor of TGFβ/Activin-Nodal signaling is contacted to the cells at a concentration of between about 1 and 20 µM, or between about 2 and 19 µM, or between about 3 and 18 µM, or between about 4 and 17 µM, or between about 5 and 16 µM, or between about 6 and 15 µM, or between about 7 and 14 µM, or between about 8 and 13 µM, or between about 9 and 12 µM, or between about 10 and 11 µM, and values in between. In certain embodiments, the one or more inhibitor of TGFβ/Activin-Nodal signaling is contacted to the cells at a concentration of about 7, 8, 9, 10, 11, 12, or 13 µM. In certain embodiments, the one or more inhibitor of TGFβ/Activin-Nodal signaling is contacted to the cells at a concentration of about 10.8 µM.

In certain embodiments, the one or more inhibitor of BMP/SMAD signaling is contacted to the cells for at least about 4, 5, 6, 7, 8, 9, or 10 or more days, for example, between about 4 and 10 days, or between about 5 and 9 days, or between about 6 and 8 days. In certain embodiments, the one or more inhibitor of BMP/SMAD signaling is contacted to the cells for up to about 4, 5, 6, 7, 8, 9, or 10 or more days. In certain embodiments, the one or more inhibitor of BMP/SMAD signaling is contacted to the cells for about 7 days. In certain embodiments, the one or more inhibitor of BMP/SMAD signaling is added every day or every other day to a cell culture medium comprising the stem cells from day 0 to day 10 (e.g., added on day 0, day 2, day 4, day 6, day 8, and day 10). In certain embodiments, the one or more inhibitor is added on days 0, 1, 3, 4, and 6.

In certain embodiments, the one or more inhibitor of BMP/SMAD signaling is contacted to the cells at a concentration of between about 50 and 500 nM, or between about 75 and 475 nM, or between about 100 and 450 nM, or between about 125 and 425 nM, or between about 150 and 400 nM, or between about 175 and 375 nM, or between about 200 and 350 nM, or between about 225 and 325 nM, or between about 250 and 300 nM, and values in between. In certain embodiments, the one or more inhibitor of BMP/SMAD signaling is contacted to the cells at a concentration of about 150, 200, 250, 300, or 350 nM. In certain embodiments, the one or more inhibitor of BMP/SMAD signaling is contacted to the cells at a concentration of about 250 nM.

In certain embodiments, the one or more activator of SHH signaling is contacted to the cells for at least about 4, 5, 6, 7, 8, 9, or 10 or more days, for example, between about 4 and 10 days, or between about 5 and 9 days, or between about 6 and 8 days. In certain embodiments, the one or more activator of SHH signaling is contacted to the cells for up to about 4, 5, 6, 7, 8, 9, or 10 or more days. In certain embodiments, the one or more activator of SHH signaling is contacted to the cells for about 7 days. In certain embodiments, the one or more activator of SHH signaling is added every day or every other day to a cell culture medium comprising the stem cells from day 0 to day 10 (e.g., added on day 0, day 2, day 4, day 6, day 8, and day 10). In certain embodiments, the one or more inhibitor is added on days 0, 1, 3, 4, and 6.

In certain embodiments, the one or more activator of SHH signaling is contacted to the cells at a concentration of between about 50 and 1000 ng/mL, or between about 100 and 950 ng/mL, or between about 150 and 900 ng/mL, or between about 200 and 850 ng/mL, or between about 250 and 800 ng/mL, or between about 300 and 750 ng/mL, or between about 350 and 700 ng/mL, or between about 400 and 650 ng/mL, or between about 450 and 600 ng/mL, or between about 500 and 550 ng/mL, and values in between. In certain embodiments, the one or more activator of SHH signaling is contacted to the cells at a concentration of about 400, 450, 500, 550, or 600 ng/mL. In certain embodiments, the one or more activator of SHH signaling is contacted to the cells at a concentration of about 500 ng/mL.

In certain embodiments, the one or more activator of Wnt signaling is contacted to the cells for at least about 4, 5, 6, 7, 8, 9, 10, 11, 12, 13, 14, 15, 16, 17, 18, 19, or 20 or more days, for example, between about 4 and 20 days, or between about 4 and 19 days, or between about 4 and 18 days, or between about 4 and 17 days, or between about 4 and 16 days, or between about 4 and 15 days, or between about 4 and 14 days, or between about 4 and 13 days, or between about 4 and 12 days, or between about 4 and 11 days, or between about 4 and 10 days, or between about 4 and 9 days, or between about 4 and 8 days, or between about 4 and 7 days, or between about 4 and 6 days, or between about 5 and 19 days, or between about 6 and 17 days, or between about 7 and 16 days, or between about 8 and 15 days, or between about 9 and 14 days, or between about 10 and 13 days. In certain embodiments, the one or more activator of Wnt signaling is contacted to the cells for up to about 4, 5, 6, 7, 8, 9, 10, 11, 12, 13, 14, 15, 16, 17, 18, 19, or 20 or more days. In certain embodiments, the one or more activator of Wnt signaling is contacted to the cells for about 12 days. In certain embodiments, the one or more activator of SHH signaling is added every day or every other day to a cell culture medium comprising the stem cells from day 0 to day 12 (e.g., added on day 0, day 2, day 4, day 6, day 8, day 10, and day 12). In certain embodiments, the one or more inhibitor is added on days 0, 1, 3, 4, 6, 7, 9, 10, and 11.

In certain embodiments, the one or more activator of Wnt signaling is contacted to the cells at a concentration of between about 0.05 and 15 µM, or between about 0.1 and 14 µM, or between about 0.5 and 13 µM, or between about 1 and 12 µM, or between about 1.5 and 11 µM, or between about 2 and 10 µM, or between about 2.5 and 9.5 µM, or between about 3 and 9 µM, or between about 3.5 and 8.5 µM, or between about 4 and 8 µM, or between about 4.5 and 7.5 µM, or between about 5 and 7 µM, or between about 5.5 and 6.5 µM, and values in between. In certain embodiments, the one or more activator of Wnt signaling is contacted to the cells at a concentration of about 0.1, 0.2, 0.3, 0.4, 0.5, 0.6, 0.7, 0.8, 0.9, or 1 µM. In certain embodiments, the one or more activator of Wnt signaling is contacted to the cells at a concentration of about 0.7 µM.

In certain embodiments, the concentration of the activator of Wnt signaling is increased at least about 2, 3, 4, 5 or 6 days after the cells are initially contacted with the Wnt activator, for example, between about 2 and 10 days, or between about 3 and 9 days, or between about 4 and 8 days, or between about 5 and 7 days. In certain embodiments, the concentration of the activator of Wnt signaling is increased up to about 2, 3, 4, 5 or 6 days after the cells are initially contacted with the Wnt activator. In certain embodiments, the cells are contacted with the increased concentration of the Wnt activator for at least about 4, 5, 6, 7, 8, 9, or 10 days or more, for example, between about 4 and 20 days, or between about 5 and 19 days, or between about 6 and 18 days, or between about 7 and 17 days, or between about 8 and 16 days, or between about 9 and 15 days, or between about 8 and 14 days, or between about 9 and 13 days, or between about 10 and 12 days. In certain embodiments, the cells are contacted with the increased concentration of the Wnt activator for up to about 4, 5, 6, 7, 8, 9, or 10 days or more. In certain embodiments, the cells are contacted with the increased concentration of the Wnt activator for about 5, 6, 7, 8, 9, 10, or 11 days. In certain embodiments, the cells are contacted with the increased concentration of the Wnt activator for about 8 days.

In certain embodiments, the concentration of the activator of Wnt signaling is increased to a concentration of between about 2 and 15 µM, or between abut 3 and 14 µM, or between about 4 and 13 µM, or between about 5 and 12 µM, or between about 6 and 11 µM, or between about 7 and 10 µM, or between about 8 and 9 µM. In certain embodiments, the concentration of the activator of Wnt signaling is increased to a concentration of between about 3 and 10 µM, or between about 5 and 10 µM. In certain embodiments, the concentration of the activator of Wnt signaling is increased to a concentration of about 3, 3.5, 4, 4.5, 5, 5.5, 6, 6.5, 7, 7.5, 8, 8.5, 9, 9.5 or 10 µM. In certain embodiments, the concentration of the activator of Wnt signaling is increased to a concentration of about 3 µM. In certain embodiments, the concentration of the activator of Wnt signaling is increased to a concentration of about 7.5 µM.

In certain embodiments, the concentration of the activator of Wnt signaling is increased from the initial concentration contacted to the cells by between about 50 and 2000%, or between about 100 and 1950%, or between about 150 and 1900%, or between about 200 and 1850%, or between about 250 and 1800%, or between about 300 and 1750%, or between about 350 and 1700%, or between about 400 and 1650%, or between about 450 and 1600%, or between about 500 and 1550%, or between about 550 and 1500%, or between about 600 and 1450%, or between about 650 and 1400%, or between about 700 and 1350%, or between about 750 and 1300%, or between about 800 and 1250%, or between about 850 and 1200%, or between about 900 and 1150%, or between about 950 and 1100%, or between about 1000 and 1050%, and values in between. In certain embodiments, the concentration of the activator of Wnt signaling is increased from the initial concentration contacted to the cells by between about 400 and 1450%, or between about 700 and 1050%, and values in between.

In certain embodiments, the concentration of the activator of Wnt signaling is increased from the initial concentration contacted to the cells by about 400%, 450%, 500%, 550%, 600%. 650%, 700%, 750%, 800%, 850%, 900%, 950%, 1000%, 1050%, or 1100% or more.

In a specific, non-limiting embodiment, the cells are contacted with one or more inhibitor of TGFβ/Activin-Nodal signaling (i.e., a first SMAD inhibitor), for example, SB431542 at a concentration of about 10.8 µM; one or more inhibitor of BMP signaling (i.e., a second SMAD inhibitor), for example, LDN193189 at a concentration of about 250 nM; one or more activator of Wnt signaling, for example, CHIR99021 at a concentration of about 0.7 µM; and one or more activator of SHH signaling at a concentration of about 500 ng/mL; wherein the cells are contacted with the inhibitors for about 7 days (i.e., Day 0 to Day 6 of culture), wherein the concentration of CHIR99021 is increased to 3 µM or 7.5 µM at day 4 of cell culture.

In certain embodiments, the cells are contacted with the one or more activator of Wnt signaling for about 11 (i.e., Day 0 to Day 11 of culture), wherein the cells are contacted with 7.5 µM of CHIR99021 from day 4 through day 11 of cell culture; or wherein the cells are contacted with 7.5 µM of CHIR99021 from day 4 through day 9 of culture, and then with 3 µM of CHIR99021 from day 10 through day 11 of cell culture.

In certain embodiments, the cells are contacted with the activators and inhibitors described herein at a concentration and for a time effective to increase a detectable level of expression of one or more of engrailed-1 (EN-1), orthodenticle homeobox 2 (OTX2), tyrosine hydroxylase (TH), nuclear receptor related-1 protein (NURR1), forkhead box protein A2 (FOXA2), and LIM homeobox transcription factor 1 alpha (LMX1A).

In certain embodiments, the cells are contacted with the activators and inhibitors described herein at a concentration and for a time effective to increase a detectable level of expression of one or more of neuron-specific class III beta-tubulin (Tuj 1), Trefoil factor family 3 (TTF3), paired-like homeodomain 3 (PITX3), achaete-scute complex (ASCL), early B-cell factor 1 (EBF-1), early B-cell factor 3 (EBF-3), transthyretin (TTR), synapsin, dopamine transporter (DAT), and G-protein coupled, inwardly rectifying potassium channel (Kir3.2/GIRK2), CD142, DCSM1, CD63 and/or CD99.

In certain embodiments, the cells are contacted with the activators and inhibitors described herein at a concentration and for a time effective to increase a detectable level of expression of one or more of marker of a DA neuron, for example, CD142, or wherein the cells are A9 type neuronal cells.

In certain embodiments, the cells are contacted with the activators and inhibitors described herein at a concentration and time effective to decrease expression of paired box protein (PAX6) and Ki67.

In certain embodiments, the cells are further contacted with DA neuron lineage specific activators and inhibitors, for example, L-glutamine, brain-derived neurotrophic factor (BDNF), glial cell-derived neurotrophic factor (GDNF), Cyclic adenosine monophosphate (cAMP), Transforming growth factor beta (TGFβ, for example, TGFβ3), ascorbic acid (AA), and DAPT (which is also known as, N-[(3,5-Difluorophenyl)acetyl]-L-alanyl-2-phenyl]glycine-1,1-dimethylethyl ester; LY-374973, N-[N-(3,5-Difluorophenacetyl)-L-alanyl-S-phenylglycine t-butyl ester; or N-[N-(3, 5-difluorophenacetyl)-L-alanyl-S-phenylglycine t-butyl ester). In certain embodiments, the cells are contacted with the foregoing DA neuron lineage specific activators and inhibitors for at least about 2, 3, 4, 5, 6, 7, 8, 9, or 10 or more days, for example, between about 2 and 20 days, between about 3 and 19 days, between about 4 and 18 days, between about 5 and 17 days, between about 6 and 16 days, between about 7 and 15 days, between about 8 and 15 days, between about 9 and 14 days, or between about 10 and 13 days. In certain embodiments, the cells are contacted with the foregoing DA neuron lineage specific activators and inhibitors for up to about 2, 3, 4, 5, 6, 7, 8, 9, or 10 or more days. In certain embodiments, the cells are contacted with the foregoing DA neuron lineage specific activators and inhibitors for about 4, 5, 6, 7, or 8 days.

In certain embodiments, the cells are contacted with L-glutamine at a concentration of between about 0.5 and 5 mM, or between about 1 and 4 mM, or between about 1.5 and 3 mM. In certain embodiments, the cells are contacted with L-glutamine at a concentration of about 2 mM.

In certain embodiments, the cells are contacted with BDNF at a concentration of between about 5 and 50 ng/mL, or between about 10 and 40 ng/mL, or between about 15 and 30 ng/mL, or between about 18 and 25 ng/mL. In certain embodiments, the cells are contacted with BDNF at a concentration of about 20 ng/mL.

In certain embodiments, the cells are contacted with AA at a concentration of between about 50 and 500 nM, or between about 100 and 400 nM, or between about 150 and 300 nM, or between about 180 and 250 nM. In certain embodiments, the cells are contacted with AA at a concentration of about 200 nM.

In certain embodiments, the cells are contacted with GDNF at a concentration of between about 5 and 50 ng/mL, or between about 10 and 40 ng/mL, or between about 15 and 30 ng/mL, or between about 18 and 25 ng/mL. In certain embodiments, the cells are contacted with GDNF at a concentration of about 20 ng/mL.

In certain embodiments, the cells are contacted with cAMP at a concentration of between about 200 and 800 nM, or between about 250 and 750 nM, or between about 300 and 700 nM, or between about 350 and 650 nM, or between about 400 and 600 nM, or between about 450 and 550 nM. In certain embodiments, the cells are contacted with cAMP at a concentration of about 500 nM.

In certain embodiments, the cells are contacted with TGFβ3 at a concentration of between about 0.01 and 5 ng/mL, or between about 0.05 and 4 ng/mL, or between about 0.1 and 3 ng/mL, or between about 0.5 and 2 ng/mL. In certain embodiments, the cells are contacted with TGFβ3 at a concentration of about 1 ng/mL.

In certain embodiments, the differentiated midbrain DA precursors are further cultured as described by U.S. Publication No. 2015/0010514, which is incorporated by reference in its entirety.

In certain embodiments, the cells prepared according to the methods described herein can be sorted, selected and isolated based on CD142 expression, or cholinergic receptor (CHRNB3) expression, for example, using flow cytometry.

In certain embodiments, the cells prepared according to the methods described herein can be further contacted with a polysialyltransferase, for example, a bacterial polysialyltransferase, such as *Neisseria meningitidis* polysialyltransferase ($PST_{Nm}$). In certain embodiments, the cells are recombinant cells expressing a recombinant polysialyltransferase.

5.3 Method of Treating Neurodegenerative Disorders

The in vitro differentiated cells that express one or markers of a midbrain DA neuron, or precursor thereof (also referred to as "stem-cell-derived midbrain DA precursors"

or "mDA" precursors) can be used for treating a neurodegenerative disorder. The presently disclosed subject matter provides for methods of treating a neurodegenerative disorder comprising administering an effective amount of the presently disclosed stem-cell-derived precursors into a subject suffering from a neurodegenerative disorder.

Non-limiting examples of a neurodegenerative disorders include Parkinson's disease, Huntington's disease, Alzheimer's disease, and multiple sclerosis.

In certain embodiments, the neurodegenerative disease is Parkinson's disease. Primary motor signs of Parkinson's disease include, for example, but not limited to, tremor of the hands, arms, legs, jaw and face, bradykinesia or slowness of movement, rigidity or stiffness of the limbs and trunk and postural instability or impaired balance and coordination.

In certain embodiments, the neurodegenerative disease is a parkinsonism disease, which refers to diseases that are linked to an insufficiency of dopamine in the basal ganglia, which is a part of the brain that controls movement. Symptoms include tremor, bradykinesia (extreme slowness of movement), flexed posture, postural instability, and rigidity. Non-limiting examples of parkinsonism diseases include corticobasal degeneration, Lewy body dementia, multiple systematrophy, and progressive supranuclear palsy.

The presently disclosed stem-cell-derived precursors can be administered or provided systemically or directly to a subject for treating or preventing a neurodegenerative disorder. In certain embodiments, the presently disclosed stem-cell-derived precursors are directly injected into an organ of interest (e.g., the central nervous system (CNS) or peripheral nervous system (PNS)). In certain embodiments, the presently disclosed stem-cell-derived precursors are directly injected into the striatum.

The presently disclosed stem-cell-derived precursors can be administered in any physiologically acceptable vehicle. Pharmaceutical compositions comprising the presently disclosed stem-cell-derived precursors and a pharmaceutically acceptable vehicle are also provided. The presently disclosed stem-cell-derived precursors and the pharmaceutical compositions comprising said cells can be administered via localized injection, orthotopic (OT) injection, systemic injection, intravenous injection, or parenteral administration. In certain embodiments, the presently disclosed stem-cell-derived precursors are administered to a subject suffering from a neurodegenerative disorder via orthotopic (OT) injection.

The presently disclosed stem-cell-derived precursors and the pharmaceutical compositions comprising said cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof. Sterile injectable solutions can be prepared by incorporating the compositions of the presently disclosed subject matter, e.g., a composition comprising the presently disclosed stem-cell-derived precursors, in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin. According to the presently disclosed subject matter, however, any vehicle, diluent, or additive used would have to be compatible with the presently disclosed stem-cell-derived precursors.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the presently disclosed stem-cell-derived precursors. This will present no problem to those skilled in chemical and pharmaceutical principles, or problems can be readily avoided by reference to standard texts or by simple experiments (not involving undue experimentation), from this disclosure and the documents cited herein.

In certain non-limiting embodiments, the cells and precursors described herein are comprised in a composition that further comprises a biocompatible scaffold or matrix, for example, a biocompatible three-dimensional scaffold that facilitates tissue regeneration when the cells are implanted or grafted to a subject. In certain non-limiting embodiments, the biocompatible scaffold comprises extracellular matrix material, synthetic polymers, cytokines, collagen, polypeptides or proteins, polysaccharides including fibronectin, laminin, keratin, fibrin, fibrinogen, hyaluronic acid, heparin sulfate, chondroitin sulfate, agarose or gelatin, and/or hydrogel. (See, e.g., U.S. Publication Nos. 2015/0159135, 2011/0296542, 2009/0123433, and 2008/0268019, the contents of each of which are incorporated by reference in their entireties). In certain embodiments, the composition further comprises growth factors for promoting maturation of the implanted/grafted cells into midbrain DA cells.

One consideration concerning the therapeutic use of the presently disclosed stem-cell-derived precursors is the quantity of cells necessary to achieve an optimal effect. An optimal effect includes, but is not limited to, repopulation of CNS and/or PNS regions of a subject suffering from a neurodegenerative disorder, and/or improved function of the subject's CNS and/or PNS.

An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the neurodegenerative disorder or pituitary disorder, or otherwise reduce the pathological consequences of the neurodegenerative disorder. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the cells administered.

In certain embodiments, an effective amount of the presently disclosed stem-cell-derived precursors is an amount that is sufficient to repopulate CNS and/or PNS regions of a subject suffering from a neurodegenerative disorder. In certain embodiments, an effective amount of the presently disclosed stem-cell-derived precursors is an amount that is sufficient to improve the function of the CNS and/or PNS of a subject suffering from a neurodegenerative disorder, e.g., the improved function can be about 1%, about 5%, about 10%, about 20%, about 30%, about 40%, about 50%, about 60%, about 70%, about 80%, about 90%, about 95%, about 98%, about 99% or about 100% of the function of a normal person's CNS and/or PNS.

The quantity of cells to be administered will vary for the subject being treated. In certain embodiments, from about $1\times10^4$ to about $1\times10^{10}$, from about $1\times10^4$ to about $1\times10^5$, from about $1\times10^5$ to about $1\times10^9$, from about $1\times10^5$ to about $1\times10^6$, from about $1\times10^5$ to about $1\times10^7$, from about $1\times10^6$ to about $1\times10^7$, from about $1\times10^6$ to about $1\times10^8$, from about $1\times10^7$ to about $1\times10^8$, from about $1\times10^8$ to about $1\times10^9$, from about $1\times10^8$ to about $1\times10^{10}$, or from about $1\times10^9$ to about $1\times10^{10}$ of the presently disclosed stem-cell-derived precursors are administered to a subject. In certain embodiments, from about $1\times10^5$ to about $1\times10^7$ of the presently disclosed stem-cell-derived precursors are administered to a subject suffering from a neurodegenerative disorder. In certain embodiments, from about $1\times10^6$ to about $1\times10^7$ of the presently disclosed stem-cell-derived precursors are administered to a subject suffering from a neurodegenerative disorder. In certain embodiments, from about $1\times10^6$ to about $4\times10^6$ of the presently disclosed stem-cell-derived precursors are administered to a subject suffering from a neurodegenerative disorder. The precise determination of what would be considered an effective dose may be based on factors individual to each subject, including their size, age, sex, weight, and condition of the particular subject. Dosages can be readily ascertained by those skilled in the art from this disclosure and the knowledge in the art.

In certain embodiments, the cells that are administered to a subject suffering from a neurodegenerative disorder for treating a neurodegenerative disorder are a population of neurons that are differentiated/maturalized from the presently disclosed stem-cell-derived midbrain DA precursors.

5.4 Kits

The presently disclosed subject matter provides for kits for inducing differentiation of stem cells. In certain embodiments, the kit comprises (a) one or more inhibitor of transforming growth factor beta (TGFβ)/Activin-Nodal signaling, (b) one or more inhibitor of BMP/SMAD signaling, (c) one or more activator of Wnt signaling, (d) one or more activator of SHH signaling, and (e) instructions for inducing differentiation of the stem cells into a population of differentiated cells that express one or more marker of a midbrain DA neuron, or precursor thereof.

In certain embodiments, the kit does not comprise one or more inhibitor of BMP/SMAD signaling.

In certain embodiments, the kit further comprises one or more activator of BMP signaling.

In certain embodiments, the instructions comprise contacting the stem cells with the inhibitor(s), activator(s) and molecule(s) in a specific sequence. The sequence of contacting the inhibitor(s), activator(s) and molecule(s) can be determined by the cell culture medium used for culturing the stem cells.

In certain embodiments, the instructions comprise contacting the stem cells with the inhibitor(s), activator(s) and molecule(s) as described by the methods of the present disclosure (see, supra, Section 5.2).

In certain embodiments, the present disclosure provides for kits comprising an effective amount of a population of the presently disclosed stem-cell-derived precursors or a composition comprising said precursors in unit dosage form. In certain embodiments, the stem-cell-derived cells are mature differentiated cells, for example, midbrain DA neurons. In certain embodiments, the kit comprises a sterile container which contains the therapeutic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In certain embodiments, the kit comprises instructions for administering a population of the presently disclosed stem-cell-derived precursors or a composition comprising thereof to a subject suffering from a neurodegenerative disorder. The instructions can comprise information about the use of the cells or composition for treating or preventing a neurodegenerative disorder. In certain embodiments, the instructions comprise at least one of the following: description of the therapeutic agent; dosage schedule and administration for treating or preventing a neurodegenerative disorder or symptoms thereof; precautions; warnings; indications; counter-indications; over dosage information; adverse reactions; animal pharmacology; clinical studies; and/or references. The instructions can be printed directly on the container (when present), or as a label applied to the container, or as a separate sheet, pamphlet, card, or folder supplied in or with the container.

6. EXAMPLES

The presently disclosed subject matter will be better understood by reference to the following Examples, which are provided as exemplary of the presently disclosed subject matter, and not by way of limitation.

6.1 Example 1 Methods of Preparing Stem Cell-Derived Midbrain Dopamine (DA) Progenitor Cells

Summary

Human embryonic stem cells (hESC) can give rise to potentially any cell type of the body. A long-term goal is the development of strategies to re-create the complete human lineage tree in vitro. The present example describes a strategy to differentiate hESC into midbrain dopamine neuron precursor cells, wherein the cells were differentiated in neurobasal (NB)/N2 media (which can optionally include E6 media) supplemented with SB431542 (TGFβ/Activin-nodal signaling inhibitor), LDN193189 (BMP/SMAD signaling inhibitor), Sonic Hedgehog (SHE), and CHIR99021 (GSK3β inhibitor that increases wingless (Wnt) signaling), wherein the concentration of CHIR99021 was increased ("bump") after the cells were initially cultured with the growth factors for four or five days. The cells were cultured with the increased concentration of CHIR99021 for seven or eight days. The cells were then cultured with the DA neuron growth factors brain-derived neurotrophic factor (BDNF), glial cell-derived neurotrophic factor (GDNF), Cyclic adenosine monophosphate (cAMP), Transforming growth factor beta 3 (TGFβ3), ascorbic acid (AA), and DAPT to produce the midbrain DA precursors.

Methods hESCs were maintained in E8/matrigel media prior to differentiation. Cells were differentiated in NB/N2 media supplemented growth factors according to the following culture strategy, wherein cells were cultured with either a 3 µM bump on day four or a 7.5 µM bump on day five.

3 µM Bump Protocol (GMP V2A)
  Day 0 (D0): hESC's were transferred from E8/matrigel media to differentiation media comprising neurobasal (NB)/N2 media supplemented with differentiation factors as follows (the D0 media also included 10 µM Y-27632 ROCK (Rho-associated, coiled-coil containing protein kinase) inhibitor to enhance survival of the cells). The cells were at a concentration of about 2 million cells/mL:
    250 nM LDN193189
    10 µM SB431542
    500 ng/mL SHH
    0.7 µM CHIR99021
  D1: The differentiation media was changed with fresh differentiation media that did not comprise Y-27632.
  D2: No media change.
  D3: Media changed as described for D1.
  D4: The differentiation media was changed with fresh differentiation media that comprised 3 µM CHIR99021 (and did not comprise Y-27632).
  D5: No media change.
  D6: Media changed as described for D4.
  D7: The differentiation media was changed with fresh media comprising NB/N2 supplemented with 3 µM CHIR99021 (and no LDN193189, SB431542, SHH or Y-27632).
  D8: No media change.
  D9: Media changed as described for D7.
  D10: The media was changed with fresh NB/B27 media comprising 3 µM CHIR99021, BDNF, GDNF, cAMP, TGFβ3, and AA.
  D11: Media changed as described for D10.
  D12: Media changed as described for D10, except the media further comprised DAPT, and did not comprise CHIR99021.
  D13-D19: Media changed as described for D12. (Culture period can be up to D27 or more, and include at least one passage at D17 or D18).
  D20: Media aspirated off cells, and cells washed and suspended in NB media, and then plated.
  Cells were then tested for expression of early midbrain DA marker combinations: 1) OTX2/EN/LMX1A and 2) PAX6/FOXA2/EN/ and NKX2.2 or NKX6.1; or late midbrain DA marker combinations: 1) TH/EN/FOXA2 and 2) LMX1A/OTX2/NURR1.
  Cells were subjected to cryopreservation or transplantation into mice.
  For transplantation into mice, cells were suspended in HBSS+HEPPES at a concentration of 150,000/microliter, wherein 5-6 million cells were grafted into immunodeficient mice.

7.5 µM Bump Protocol (GMP V2B)
  Day 0 (D0): hESC's were transferred from E8/matrigel media to differentiation media comprising neurobasal (NB)/N2 media supplemented with differentiation factors as follows (the D0 media also included 10 µM Y-27632 ROCK (Rho-associated, coiled-coil containing protein kinase) inhibitor to enhance survival of the cells). The cells were at a concentration of about 2 million cells/mL:
    250 nM LDN193189
    10 µM SB431542
    500 ng/mL SHH
    0.7 µM CHIR99021
  D1: The differentiation media was changed with fresh differentiation media that did not comprise Y-27632.
  D2: No media change.
  D3: Media changed as described for D1.
  D4: No media change.
  D5: The differentiation media was changed with fresh differentiation media that comprised 7.5 µM CHIR99021 (and did not comprise Y-27632).
  D6: No media change.
  D7: The differentiation media was changed with fresh media comprising NB/N2 supplemented with 7.5 µM CHIR99021 (and no LDN193189, SB431542, SHH or Y-27632).
  D8: No media change.
  D9: Media changed as described for D7.
  D10: The media was changed with fresh NB/B27 media comprising 3 µM CHIR99021, BDNF, GDNF, cAMP, TGFβ3, and AA.
  D11: Media changed as described for D10.
  D12: Media changed as described for D10, except the media further comprised DAPT, and did not comprise CHIR99021,
  D13-D19: Media changed as described for D12. (Culture period can be up to D27 or more, and include at least one passage at D17 or D18).
  D20: Media aspirated off cells, and cells washed and suspended in NB media, and then plated.
  Cells were tested for expression of early midbrain DA marker combinations: 1) OTX2/EN/LMX1A and 2) PAX6/FOXA2/EN/ and NKX2.2 or NKX6.1; or late midbrain DA marker combinations: 1) TH/EN/FOXA2 and 2) LMX1A/OTX2/NURR1.
  Cells were subjected to cryopreservation or transplantation into mice.

For transplantation into mice, cells were suspended in HBSS+HEPPES at a concentration of 150,000/microliter, wherein 5-6 million cells were grafted into immunodeficient mice.

Results

Kriks et al., Nature. 2011 Nov. 6; 480(7378):547-51, describes a protocol for differentiation hESCs into midbrain DA cells by culturing the cells in KSR media comprising dual SMAD inhibition, SHH activation, and Wnt activation (without a "bump" as described below). However, KSR media is undefined, and the cells produced using the differentiation protocol perform poorly in vivo after transplantation. The cells differentiated according to the present example utilize a culture protocol that includes dual SMAD inhibition (via SB431542 and LDN193189), SHE activation and Wnt activation in NB/N2 media, wherein the concentration of Wnt is increased to between 5-10 µM from a 0.7 µM baseline concentration at D4 or D5 of culture (i.e., a Wnt "bump").

As shown in FIG. 1, differentiating hESCs according to the method described by Kriks et al. in KSR media (Non-GMP) or in E8/NB/N2 media (GMP V1) produced midbrain DA neurons;

however, neurons of other brain regions were also produced. When the cells were cultured in E8/NB/N2 media according to the methods of the present example utilizing a 7.5 µM (or 5-10 µM) Wnt bump at D4-D10, midbrain DA cells were specifically produced.

As shown in FIG. 2, differentiating hESCs according to the method described by Kriks et al. in KSR media (Non-GMP) or in E8/NB/N2 media (GMP V1) both produced cells expressing similar levels of PAX6, TH, NURR1, FOXA2, and LMX1A. However, the cells produced using either media exhibited poor survival when transplanted into rodents.

When the hESCs were differentiated using E8/NB/N2 media and a 3 µM (GMP V2A) or 7.5 µM (GMP V2B) Wnt bump, the cells also expressed similar levels of PAX6, TH, NURR1, FOXA2, and LMX1A as the Kriks et al. protocol using KSR (Non-GMP) or E8/NB/N2 (GMP V1). However, the cells differentiated according to the GMP V2A or GMP V2B protocols expressed higher levels of the midbrain DA marker EN-1 (FIG. 3). FIG. 4 describes other midbrain DA markers that can be used to identify differentiated cells.

hESCs differentiated using the Kriks et al. protocol in E8/NB/N2 media sometimes resulted in good survival of DA cells expressing Hncam, FOXA2, and TH in vivo after differentiation for 25 days and transplantation into unlesioned, immunocompromised mice. Grafts were examined 4 weeks after transplantation. However, the cells exhibited dense patches of Hncam expression, which were also positive for PAX6, indicating a neural progenitor status (FIG. 5). hESCs cultured according to the GMP V2A (3 µM bump) or GMP V2B (7.5 µM bump) produced DA cells expressing increased NURR1, LMX1A, EN-1, and TH levels in vitro (FIG. 6A), and did not express PAX6 (FIG. 7). Furthermore, midbrain DA cells differentiated using the GMP V2B (7.5 µM bump) protocol that were transplanted into the striatum of unlesioned, immunocompromised mice exhibited enhanced fiber outgrowth and expression of hNCAM and TH 3-weeks post grafting, without Hncam patches (FIG. 6B). Additionally, when cells had been cryopreserved prior to transplantation, the cells exhibited fiber outgrowth that was similar to fiber outgrowth of cells grafted into mice that had not been previously cryopreserved (FIG. 8).

As shown in FIG. 9A-B, cells prepared according to the GMP V2A or GMP V2B protocols can be successfully sorted based on CD142 expression. Additionally, midbrain DA cells cultured according to the methods described by Kirks et al. in KSR media, and sorted based on CD142 expression, were grafted into mice and non-human primates. As shown by FIG. 10A-B, these cells survive short term when transplanted into mice (30-days post transplantation) and non-human primates (1-year post-transplantation), and contain many TH expressing neurons.

Figure 11A:
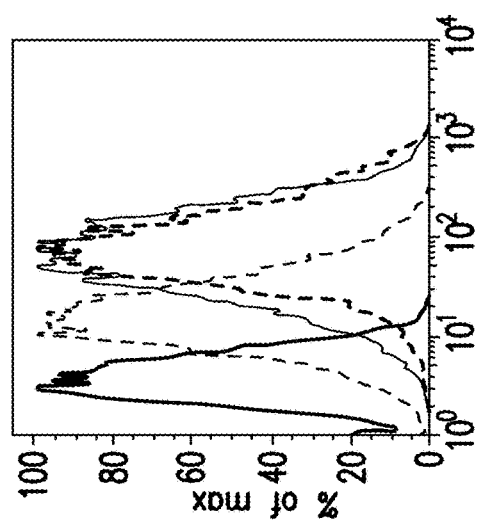
Figure 11B:
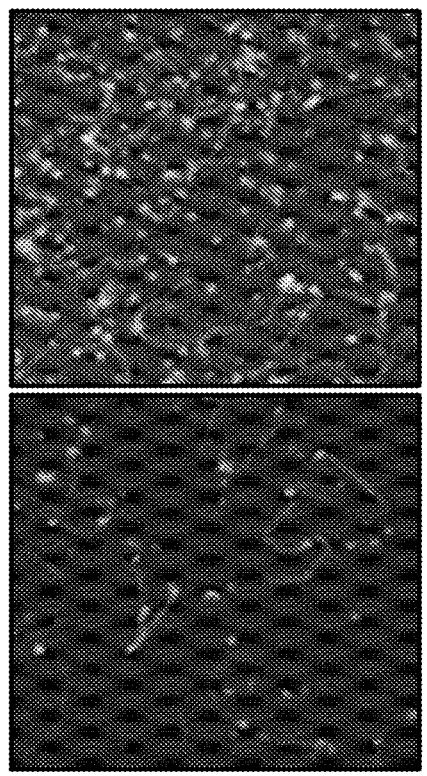
Figure 11C:
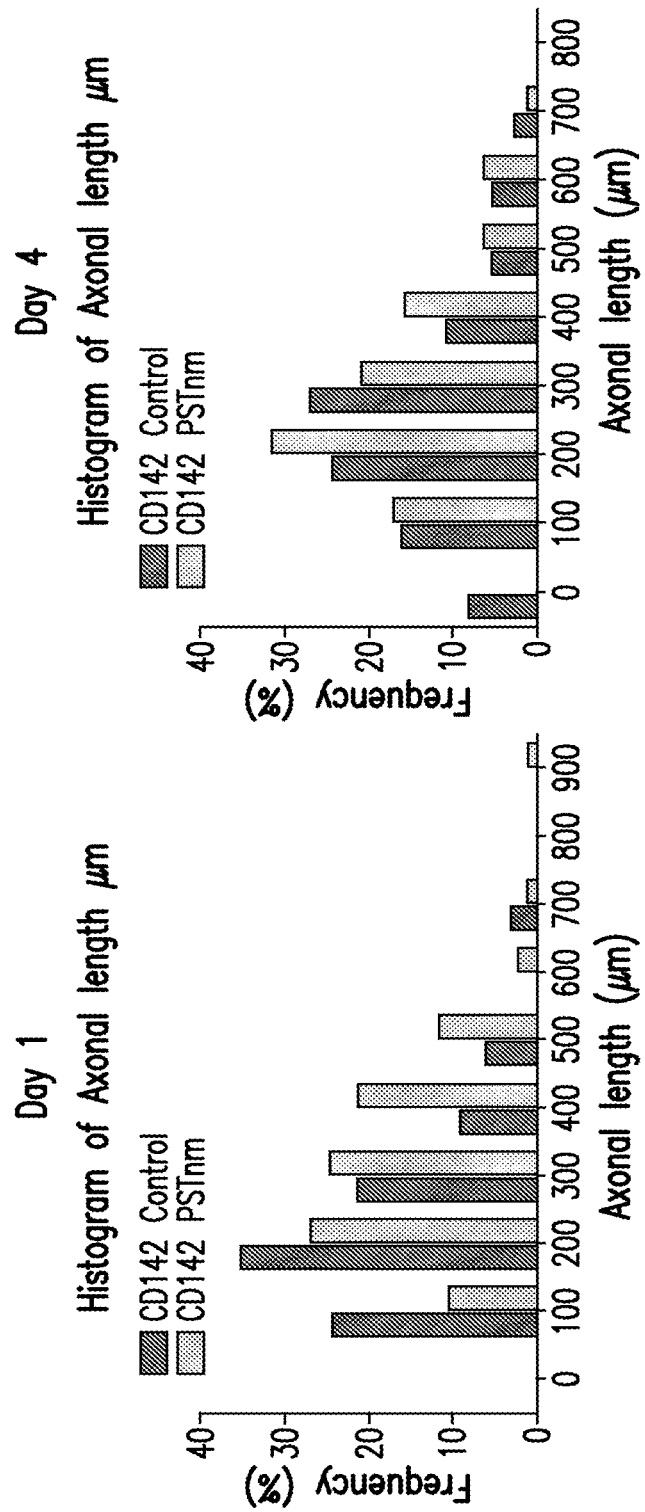
Figure 11D:
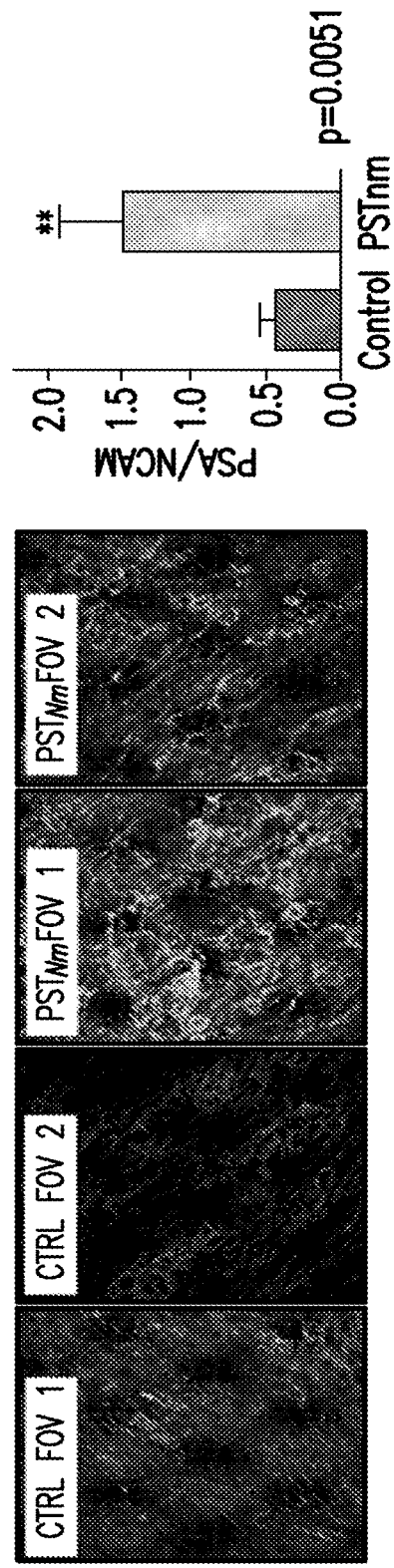

Furthermore, increased levels of polysialylation due to polysialyltransferase treatment (*Neisseria meningitidis* polysialyltransferase ($PST_{Nm}$)) of differentiated midbrain DA cells were stable after a freeze-thaw cycle, and after transplantation into mice in vivo. Additionally, CD142 cell sorting was not affected by polysialyltransferase treatment (FIGS. 11A, B and D). Further, while untreated cells have about 10% of the neurons without noticeable outgrowth in vivo after transplant into mice, none of the polysialyltransferase treated cells had axons with a length of less than 100 µm 2-weeks after grafting of the mDA cells in the striatum of mice (FIG. 11C).

6.2 Example 2 Methods of Preparing Stem Cell-Derived Midbrain Dopamine (DA) Progenitor Cells Summary The present example provides a modified version of the GMP V2A differentiation protocol described by Example 1.

hESCs were maintained in E8/matrigel media prior to differentiation. Cells were differentiated in NB/N2/B27 media supplemented with growth factors according to the following culture strategy, wherein cells were cultured with a 7.5 µM bump on day four.

7.5 µM Bump Protocol (Modification of GMP V2B)
  Day 0 (D0): hESC's were transferred from E8/matrigel media to differentiation media comprising neurobasal (NB)/N2/B27 media supplemented with differentiation factors as follows (the D0 media also included 10 µM Y-27632 ROCK (Rho-associated, coiled-coil containing protein kinase) inhibitor to enhance survival of the cells). The cells were at a concentration of about 750 million cells/L:
    2 mM L-glutamine
    250 nM LDN193189
    10.8 µM SB431542
    500 ng/mL SHH
    0.7 µM CHIR99021
  D1: The differentiation media was changed with fresh differentiation media that did not comprise Y-27632.
  D2: No media change.
  D3: Media changed as described for D1.
  D4: The differentiation media was changed with fresh differentiation media that comprised 7.5 µM CHIR99021 (and did not comprise Y-27632).
  D5: No media change.
  D6: Media changed as described for D4.
  D7: The differentiation media was changed with fresh media comprising NB/N2/B27 supplemented with 2 mM L-glutamine and 7.5 µM CHIR99021 (and no LDN193189, SB431542, SHH or Y-27632).
  D8: No media change.
  D9: Media changed as described for D7.
  D10: The media was changed with fresh NB/B27 media comprising 2 mM L-glutamine, 3 µM CHIR99021, 20 ng/mL BDNF, 20 ng/mL GDNF, 500 nM cAMP, 1 ng/mL TGFβ3, and 200 nM AA.

D11: Cell passage and media changed as described for D10 to achieve a concentration of 1.5 billion cells/L.

D12: Media changed as described for D10, except the media further comprised 10 μM DAPT, and did not comprise CHIR99021.

D13-D15: Maturation media. Media changed as described for D12.

D16: Cells harvested and cryopreserved in NB.

Methods 5.0 Reagents and Materials
5.1 Texwipe Sterile TechniSat Presaturated Wipers (Fisher, Cat #19-003-239) or equivalent
5.2 Centrifugation tubes (Fisher, Cat #05-538-51 for 15 mL; Fisher, Cat #05-538-49 for 50 mL) or equivalents
5.3 Tissue culture plates (Fisher, Cat #08-772-24 for 15 cm) or equivalent
5.4 Tissue culture flasks (Fisher, Cat #13-680-65 for 75 $cm^2$; Fisher, Cat #12-565-221 for 225 $cm^2$) or equivalent
5.5 Sterile polystyrene serological pipettes (Fisher, Cat #13-675-47 for 2 mL; Fisher, Cat #13-678-11D for 5 mL; Fisher, Cat #13-678-11E for 10 mL; Fisher, Cat #13-678-11 for 25 mL; Fisher, Cat #13-678-11F; Fisher, Cat #13-675-73 for 100 mL) or equivalents
5.6 Sterile aspirating pipettes (Fisher, Cat #13-678-20D) or equivalent
5.7 zCellometer counting slides (Nexcelom, Cat # CHT4-PD-100-003) or equivalent
5.8 Sterile pipet tips (Fisher, Cat #21-403-00 for 20 μL; Fisher, Cat #21-403-01 for 200 μL; Fisher, Cat #21-403-02 for 1000 μL) or equivalents
5.9 Cryovials (Fisher, Cat #12-565-164N) or equivalent
5.10 CryoColor Code Cap Inserts (Fisher, Cat #12-565-242 for White; Fisher, Cat #12-565-180 for Assorted Colors) or equivalents
5.11 Cell strainer (Fisher, Cat #08-771-1 for 40 μM) or equivalent
5.12 AOPI (Nexcelom, Cat # CS2-0106-5 mL)
5.13 DMEM/F-12 (Life Technologies, Cat #11320)
5.14 Accutase® Cell Detachment Solution (Innovative Cell Technology, Cat # AT104)
5.15 Geltrex™ LDEV-free reduced growth factor (Life Technologies, Cat # A14132-01)
5.16 CTS™ (Cell Therapy Systems) DPBS without calcium chloride without magnesium chloride (Life Technologies, Cat # A1285601)
5.17 B27 (w/o Vitamin A) (Life Technologies, Cat #12587-010)
5.18 N2 Supplement B (Stem Cell Technologies, Cat #07156)
5.19 Neurobasal Medium (Life Technologies, Cat #21103049)
5.20 50 mg/mL Gentamicin [Optional] (Life Technologies, Cat #15750078) 5.21 500 μM LDN 193189 (SSCRF-RP-011)
5.22 10.8 mM SB431542 (SSCRF-RP-013)
5.23 100 μg/mL Shh (SSCRF-RP-014)
5.24 15 mM CHIR99021 (SSCRF-RP-004)
5.25 10 μg/mL BDNF (SSCRF-RP-003)
5.26 10 mM Y-27632 (SSCRF-RP-016)
5.27 100 mM Ascorbic Acid (SSCRF-RP-002)
5.28 10 μg/mL GDNF (SSCRF-RP-007)
5.29 100 mM dbcAMP (SSCRF-RP-006)
5.30 2 μg/mL TGF-beta 3 (SSCRF-RP-015)
5.31 10 mM DAPT (SSCRF-RP-005)
5.32 4 mM HCl (SSCRF-RP-008)
5.33 15 mg/mL Poly-L-Ornithine (SSCRF-RP-012)
5.34 1 mg/mL Human Fibronectin (SSCRF-RP-001)
5.35 1 mg/ml Cultrex Mouse Laminin I (SSCRF-RP-010)
5.36 Essential 8™ Medium (SSCRF-FR-002)
5.37 200 mM L-Glutamine (SSCRF-RP-009)

6.0 Equipment
6.1 Gilson adjustable pipettors (Pipetman-p1000, p200, p20, p10, p2) or equivalents
6.2 Integra Pipetteboy Pro Pipetaid Device or equivalent
6.3 Cellometer® Vision System
6.4 $CO_2$ Incubator (Nuaire IR Autoflow $CO_2$ water-jacked incubator) or equivalent
6.5 Sorvall Legend XTR Centrifuge (Thermo Scientific, Cat #75004520) or equivalent
6.6 CryoMed Controlled-Rate Freezer (Thermo Scientific, Cat #7450) or equivalent
6.7 Inverted Microscope (Olympus CK2) or equivalent
6.8 Biological Safety Cabinet (Baker SterileGARD Class II) or equivalent 7.0 Procedure
7.1 Day before Differentiation Initiation: Geltrex Thaw
  7.1.1 Thaw 6×5 mL frozen Geltrex™ vials at 4° C. overnight or until no ice crystals remain.
7.2 Day 0: hESC feed and Geltrex coating
  7.2.1 Replenish all WA09 hESC cultures with fresh E8 medium.
  7.2.2 Label 48×T75 flasks with the Batch Record # and an incrementing number. Perform each task hereafter sequentially.
  7.2.3 Make a 1:30 mixture of Geltrex™:DMEM/F12.
    7.2.3.1 Add 870 mL cold DMEM/F12 to 1 L bottle.
    7.2.3.2 Carefully add 30 mL Geltrex™. Wash each Geltrex™ vial once with DMEM/F12 from bottle to recover most of the product.
    7.2.3.3 Once done, cap tightly and invert to mix Geltrex with medium. Carefully swirl occasionally between uses to prevent settling.
  7.2.4 Record the time that Geltrex™ coating started.
  7.2.5 Sequentially coat each T75 vessel with 15 mL Geltrex™
  7.2.6 Record the time that Geltrex™ incubation began.
  7.2.7 Incubate in hood at room temperature for 2-3 hours.
  7.2.8 Record the time that aspiration starts.
  7.2.9 Following incubation, aspirate Geltrex™ and add 15 mL plain Neurobasal. Leave vessels at room temperature until cells are ready to plate.
  7.2.10 Record the time that Geltrex™ was withdrawn from vessels.
7.3 Day 0: Cell Set up and Induction
NOTE: 7.3 can be performed simultaneously by 2 independent operators per production suite. Two suites can process simultaneously to reduce processing time. Product must be pooled before plating to ensure homogeneity.
NOTE: If yield is higher than required, only 48 flasks can be plated. If yield is less than 48 flasks, the run is aborted.
  7.3.1 Before beginning, Accutase® one single vessel to use for OCT4+ QC (SSCRF-SOP-107) and cDNA production (SSCRF-SOP-109) and to assess yield.
    7.3.1.1 Find representative plate based on density, colony size and distribution of colonies over surface.

7.3.1.2 Aspirate the medium from cells and add Accutase®.
   7.3.1.2.1 15 mL per T225 flask
   7.3.1.2.2 10 mL per 15 cm dish
7.3.1.3 Incubate cells at 37° C. for 20-30 minutes.
7.3.1.4 Using a 10 mL pipet, dislodge and triturate cells into a homogenous suspension.
7.3.1.5 Pipet into a 50 mL conical, and add 10 mL E8 medium (20 mL total).
7.3.1.6 Centrifuge at 200×g for 5 minutes at room temperature.
7.3.1.7 Aspirate medium, and add 5 mL E8 medium.
7.3.1.8 Perform a cell count (see 7.3.20)
7.3.1.9 Aliquot $3 \times 10^6$ cells into a cryotube labeled SSCRF-SOP-109 (cDNA production for QC).
7.3.1.10 Aliquot $3 \times 10^6$ cells into a cryotube labeled SSCRF-SOP-107 (OCT4 measurement).
7.3.1.11 Submit QC tubes to separate operator to bring to QC lab.
7.3.2 Prepare 2.5 L of NB/N2/B27 containing 2 mM L-glut, 250 nM LDN193189, 10.8 μM SB431542, 500 ng/mL Shh, 0.7 μM CHIR and 10 μM Y-27632.
7.3.3 Record the input WA09#(batch #) and associated data into the batch record.
7.3.4 Work sequentially and one-by-one in batches of 12 vessels.
   NOTE: This is per operator.
7.3.5 Record the time aspiration began.
7.3.6 Remove 12 vessels of WA09 hESCs from the incubator, aspirate the media from cells and add Accutase®:
   7.3.6.1 15 mL per T225 flask
   7.3.6.2 10 mL per 15 cm dish
7.3.7 Incubate cells at 37° C. for 20-30 minutes.
7.3.8 Record the Accutase® incubation start time on the batch record.
7.3.9 Begin assembling 12 [T225] or 6 [15 cm]×50 mL conical tubes.
7.3.10 Record the Accutase® incubation end time on the batch record.
7.3.11 Using a 10 mL pipet, wash the Accutase® over the surface of each vessel ~5-10 times to dislodge and triturate cells until no clumps are visible.
7.3.12 Transfer dissociated cells in Accutase® to 50 mL conical.
7.3.13 Wash surface of dry vessel with fresh E8 medium (using volume equal to Accutase®) to recover remaining cells, and add to conical with cells Accutase®.
   NOTE: For example, a T225 flask that had 15 mL Accutase® is transferred into a conical. The dry flask is then washed with 15 mL of E8 medium, and the recovered cells-E8 added to the conical containing 15 mL Accutase®-cells (total 30 mL). A 15 cm dish containing 10 mL Accutase® is transferred into a conical, then washed with 10 mL fresh E8 (total 20 mL). Two 15 cm dishes can be pooled in one conical (total 40 mL).
   NOTE: If possible, a live sample should also be cryopreserved for archival purposes. Live samples can be frozen down as single cells using FreSR-S and the cryopreservation protocol in QC lab "USER1".
7.3.14 Centrifuge cells for 5 minutes at 200×g at room temperature.
7.3.15 Aspirate media and gently resuspend each pellet into 10 mL with fresh plain Neurobasal.
7.3.16 Pool 3 tubes into a fresh 50 mL conical (giving total of 2×50 mL conicals per batch).
7.3.17 Centrifuge cells for 5 minutes at 200×g at room temperature.
7.3.18 Aspirate media and gently resuspend using a total of 5 ml NB/N2/B27 containing 2 mM L-glut, 250 nM LDN193189, 10.8 μM SB431542, 500 ng/mL Shh, 0.7 μM CHIR and 10 μM Y-27632. Place at 4° C. until all vessels have been processed.
7.3.19 Once all vessels have been processed, pool all cells and bring up to 200 mL.
7.3.20 Count pooled cells:
   7.3.20.1 Make a known dilution of cells in plain Neurobasal (without growth factors).
   7.3.20.2 Mix 20 uL of diluted cells with 20 uL of AOPI.
   7.3.20.3 Load 20 uL of cell/AOPI mixture onto Cellometer® slide.
   7.3.20.4 Input the slide into the slot.
   7.3.20.5 Choose the program file 'hES Cells AOPI'
   7.3.20.6 Provide a file name using the following format "DA01 Lot # MMDDYY d0"
   7.3.20.7 Enter dilution value.
   7.3.20.8 Using the F1 channel, focus the cells using the knob on the right side of the machine.
   7.3.20.9 Once focused hit 'Count'
7.3.21 Record the total number of viable and non-viable cells/mL, total number of cells, and % viability
7.3.22 Aliquot $3 \times 10^6$ cells into a cryotube labeled MICR-CULT-SOP-1634 (sterility). Aliquot $3 \times 10^6$ cells into a cryotube labeled PT-OP-7020 (mycoplasma). Bring each up to 1 mL before submission, and send with separate operator for processing.
7.3.23 Adjust the cell concentration to 750 million cells per 1 L (need 2 L total).
   7.3.23.1 Calculate the volume needed to achieve 750 million cells.
   7.3.23.2 Remove volume calculated from each 1 L bottle of NB/N2/B27 containing 2 mM L-glut, 250 nM LDN193189, 10.8 μM SB431542, 500 ng/mL Shh, 0.7 μM CHIR and 10 μM Y-27632.
   7.3.23.3 Add calculated volume containing 750 million cells to each 1 L bottle.
7.3.24 Sequentially manipulate each T75 flask, one at a time.
7.3.25 Aspirate the plain Neurobasal medium from Geltrex™-coated flask.
7.3.26 Carefully add 40 mL of cell suspension to each T75.
   NOTE: Be sure to carefully suspend cells before pipetting.
7.3.27 Gently rock flask to evenly coat surface with cells.
   NOTE: cell distribution can be verified on microscope.
7.3.28 Let sit for 10-15 minutes in hood without disturbing.
7.3.29 Carefully move flasks to incubator.
7.3.30 Incubate overnight at 37° C. with 5% $CO_2$.
7.4 Day 1: Feed (0.7 μM CHIR)
7.4.1 Control Point: Check confluency of the flasks indicated on BR. Cultures should be 100% confluent. Note the confluence of the indicated flasks.
7.4.2 Sequentially manipulate each T75 flask, one at a time.

7.4.3 Aspirate existing media and gently add 40 mL per T75 NB/N2/B27 media containing 2 mM L-glut, 250 nM LDN193189 and 10.8 μM SB 431542, 500 ng/mL SHH and 0.7 μM CHIR99021.

7.5 Day 2: NO MEDIUM CHANGE 7.6 Day 3: Feed (0.7 μM CHIR)

7.6.1 Sequentially manipulate each T75 flask, one at a time.

7.6.2 Aspirate existing media and gently add 40 mL NB/N2/B27 media containing 2 mM L-glut, 250 nM LDN193189 and 10.8 μM SB431542, 500 ng/mL SHH and 0.7 μM CHIR99021.

7.7 Day 4: Feed (7.5 μM CHIR BUMP)

7.7.1 Sequentially manipulate each T75 flask, one at a time.

7.7.2 Aspirate existing media and gently add 40 mL of NB/N2/B27media containing 2 mM L-glut, 250 nM LDN193189 and 10.8 μM SB431542, 500 ng/mL SHH and 7.5 μM CHIR.

7.8 Day 5: NO MEDIUM CHANGE 7.9 Day 6: Feed (7.5 μM CHIR)

7.9.1 Sequentially manipulate each T75 flask, one at a time.

7.9.2 Aspire existing media and gently add 40 mL NB/N2/B27 media containing 2 mM L-glut, 250 nM LDN193189 and 10.8 μM SB431542, 500 ng/mL SHH and 7.5 μM CHIR99021.

7.10 Day 7: LDN, SB and SHH Withdrawal 7.10.1 Sequentially manipulate each T75 flask, one at a time.

7.10.2 Aspire existing media and gently add 40 mL NB/N2/B27 media containing 2 mM L-glut and 7.5 μM CHIR99021.

7.11 Day 8: NO MEDIUM CHANGE 7.12 Day 9: Feed (7.5 nM CHIR) and PO coating 7.12.1 Feed 7.5 μM CHIR:
  7.12.1.1 Sequentially manipulate each T75 flask, one at a time.
  7.12.1.2 Aspirate existing media and gently add 40 mL NB/N2/B27 media containing 2 mM L-glut and 7.5 μM CHIR99021.

7.12.2 PO coating:
  7.12.2.1 Label each T75 flask with the Batch Record # and an incrementing number. Perform each task sequentially.
  7.12.2.2 Coat 48×T75s with 15 mL per flask of 15 μg/mL Poly-L-Ornithine in DPBS.
    NOTE: 720 mL required but make 800 mL for overage.
  7.12.2.3 Incubate at 37° C. with 5% $CO_2$ overnight.

7.13 Day 10: Feed (3 μM CHIR no DAPT) and F/L coating 7.13.1 Feed plates with 3 μM CHIR.
  7.13.1.1 Sequentially manipulate each T75 flask, one at a time.
  7.13.1.2 Aspire existing media and gently add 40 mL NB/B27 media containing 2 mM L-glut, 20 ng/mL BDNF, 200 nM AA, 20 ng/mL GDNF, 500 nM cAMP, 1 ng/mL TGFβ3 and 3 CHIR99021.

7.13.2 F/L coating:
  7.13.2.1 Flasks can be processed in batches of 4.
  7.13.2.2 Aspirate, then add 15 mL of DPBS.
  7.13.2.3 Gently rock to wash, then repeat two more times for a total of 3×DPBS washes.
  7.13.2.4 Aspirate, then add 15 mL of 2 μg/mL Fibronectin/laminin in DPBS.
    NOTE: 720 mL required but make 800 mL for overage.
  7.13.2.5 Incubate plates at 37° C. at 5% $CO_2$ overnight.

7.14 Day 11: PASSAGE

NOTE: 7.14 can be performed simultaneously by 2 independent operators per production suite. Two suites can process flasks simultaneously to reduce processing time. Product must be pooled before plating to ensure homogeneity.

NOTE: If yield is higher than required, only 48 flasks can be passaged. If yield is less than $1\times10^9$ total cells, the batch can be aborted.

7.14.1 Prepare 2.5 L of NB/B27 media containing 2 mM L-glut, 20 ng/mL BDNF, 200 nM AA, 20 ng/mL GDNF, 500 nM cAMP, 1 ng/mL TGFβ3 and 3 μM CHIR99021.

7.14.2 Work sequentially and one-by-one in batches of 12 vessels.

7.14.3 Carefully remove flasks from hood, arrange sequentially and record when aspirations begin.

7.14.4 Aspirate existing media and add 5 mL of Accutase® per T75.

7.14.5 Record incubation start time after last Accutase® addition.

7.14.6 Incubate at 37° C. for 30-40 minutes.

7.14.7 Aspirate Fibronectin/Laminin coating to get wells as dry as possible and leave flasks open under hood until dry.

7.14.8 Sequentially label 50 mL conicals to match the T75 flasks being passaged.

7.14.9 In the hood, using careful sterile technique, set up a 40 μm blue cell strainer in one of the labeled 50 mL conical per flask.

7.14.10 Once incubation time has elapsed, record incubation stop time.

7.14.11 Remove plates from incubator.

7.14.12 Using a 10 mL pipet, pipet cells ~5-10 times with force to break up clusters.

7.14.13 Pipet triturated cells carefully through the 40 μM filter.

7.14.14 Add 15 mL plain Neurobasal medium to the dry flask to recover cells left behind.

7.14.15 Add Neurobasal containing recovered cells to 40 μM filter.
  NOTE: two vessels can be processed into the same tube at this step.

7.14.16 Carefully remove filter and discard. Cap tube.

7.14.17 Repeat process for each T75 flask.

7.14.18 Centrifuge cells for 5 minutes at 200×g at room temperature.

7.14.19 Aspirate medium and resuspend each pellet in 10 mL plain Neurobasal.

7.14.20 Combine the pellets from no more than 4 tubes into a 50 mL conical tube.

7.14.21 Centrifuge cells for 5 minutes at 200×g at room temperature.

7.14.22 Aspirate medium and resuspend each pellet in 10 mL NB/B27 media containing 2 mM L-glut, 20 ng/mL BDNF, 200 nM AA, 20 ng/mL GDNF, 500 nM cAMP, 1 ng/mL TGFβ3 and 3 μM CHIR99021.
  NOTE: Cells can be stored at 4° C. if more vessels need to be processed.

7.14.23 Once all vessels have been processed, pool all cells and bring final volume up to 200 mL using NB/B27 media containing 2 mM L-glut, 20 ng/mL BDNF, 200 nM AA, 20 ng/mL GDNF, 500 nM cAMP, 1 ng/mL TGFβ3 and 3 μM CHIR99021

7.14.23.1 Make a known dilution of cells in plain Neurobasal medium.
7.14.23.2 Mix 20 uL of diluted cells with 20 uL of AOPI.
7.14.23.3 Load 20 uL of cell/AOPI mixture onto Cellometer® slide.
7.14.23.4 Insert the slide into Cellometer®.
7.14.23.5 Choose the program file 'mDA Neurons AOPI'
7.14.23.6 Provide a file name using the following format "DA01 Lot # MMDDYY d11"
7.14.23.7 Enter the dilution value.
7.14.23.8 Using the F1 channel, focus the cells using the knob on the right side of the machine.
7.14.23.9 Once focused hit 'Count'
7.14.24 Record the total number of viable and non-viable cells/mL, total number of cells, and % viability.
7.14.25 Aliquot $3\times10^6$ cells into a cryotube labeled SSCRF-SOP-109 (cDNA production for QC).
7.14.26 Aliquot $3\times10^6$ cells into a cryotube labeled PT-OP-7020 (mycoplasma). Bring up to 1 mL before submission.
7.14.27 Aliquot $3\times10^6$ cells into a cryotube labeled MICR-CULT-SOP-1634 (sterility). Bring up to 1 mL before submission.
NOTE: If possible, a sample should also be submitted to cryopreserve a live sample for archive. Live samples can be frozen down as single cells using Stem-Cellbanker® and the cryopreservation protocol "USER1" in QC Lab.
7.14.28 Send all QC tubes with separate operator for processing according to associated SOPs.
7.14.29 Adjust the cell concentration to 1.5 billion cells per 1 L (need 2 L total).
7.14.29.1 Calculate the volume needed to achieve 1.5 billion cells.
7.14.29.2 Remove volume calculated from each 1 L bottle of NB/B27 media containing 2 mM L-glut, 20 ng/mL BDNF, 200 nM AA, 20 ng/mL GDNF, 500 nM cAMP, 1 ng/mL TGFβ3 and 3 µM CHIR99021.
7.14.29.3 Add calculated volume containing 1.5 billion cells to each 1 L bottle.
NOTE: If the cell yield is less than $3\times10^9$ but greater than $1\times10^9$, calculate the number of mL needed to bring the cells to a final concentration of $1.5\times10^6$ cells/mL and plate as many flasks as possible.
7.14.30 Add 40 mL of cell suspension to each T75 ($60\times10^6$ cells total).
NOTE: Be sure to carefully suspend cells before pipetting.
7.14.31 Carefully rock plates to ensure even cell suspension.
7.14.32 Let the plates incubate at room temp for 10 minutes.
7.14.33 Carefully move flasks to incubator.
NOTE: spot check flasks on microscope to ensure even coating.
7.14.34 Incubate plates at 37° C. at 5% $CO_2$ overnight.
7.15 Feed Day 12 (CHIR withdrawal, DAPT addition [Maturation Medium])
7.15.1 Control Point: Spot check confluence of the flasks and record on BR.
Cultures should be 100% confluent. Note the confluence of the indicated flasks.
NOTE: Maturation Medium may be used the following day in the event that the maximum number of flasks is not achieved during passage.
7.15.2 Sequentially manipulate each T75 flask, one at a time.
7.15.3 Aspirate existing media and gently add NB/B27 media containing 2 mM L-glut, 20 ng/mL BDNF, 200 nM AA, 20 ng/mL GDNF, 500 nM cAMP, 1 ng/mL TGFβ3 and 10 µM DAPT to each T75 flask.
7.16 Day 13 (Maturation Medium)
7.16.1 Sequentially manipulate each T75 flask, one at a time.
7.16.2 Aspirate existing media and gently add NB/B27 media containing 2 mM L-glut, 20 ng/mL BDNF, 200 nM AA, 20 ng/mL GDNF, 500 nM cAMP, 1 ng/mL TGFβ3 and 10 µM DAPT to each T75 flask.
7.17 Day 14 (Maturation Medium)
7.17.1 Sequentially manipulate each T75 flask, one at a time.
7.17.2 Aspirate existing media and gently add NB/B27 media containing 2 mM L-glut, 20 ng/mL BDNF, 200 nM AA, 20 ng/mL GDNF, 500 nM cAMP, 1 ng/mL TGFβ3 and 10 µM DAPT to each T75 flask.
7.18 Day 15 (Maturation Medium)
7.18.1 Sequentially manipulate each T75 flask, one at a time.
7.18.2 Aspirate existing media and gently add NB/B27 media containing 2 mM L-glut, 20 ng/mL BDNF, 200 nM AA, 20 ng/mL GDNF, 500 nM cAMP, 1 ng/mL TGFβ3 and 10 µM DAPT to each T75 flask.
7.19 Day 16: Cell Harvest and Cryopreservation
NOTE: 7.14 can be performed simultaneously by 2 independent operators per production suite. Two suites can process flasks simultaneously to reduce processing time. Product must be pooled before plating to ensure homogeneity.
7.19.1 Sequentially label and chill all cryotubes at 4° C.
7.19.2 Sequentially label boxes with lot # and tube range.
7.19.3 Note time before beginning aspiration.
7.19.4 Working sequentially in batches of 12, aspirate existing media from flasks and add 5 mL Accutase® per T75.
7.19.5 Record incubation start time.
7.19.6 Incubate at 37° C. for 30-40 minutes.
7.19.7 In the hood, set up a 40 µm blue cell strainer in a 50 mL conical (1 conical for every 2 T75 flasks).
7.19.8 Remove flask from incubator after incubation, record time in batch record.
7.19.9 Using a 10 mL pipet, pipet ~5-10 times until clusters are no longer visible.
7.19.10 Transfer cell suspension carefully through 40 µM filter.
7.19.11 Add 15 mL Neurobasal medium to dry flask to recover cells.
7.19.12 Transfer Neurobasal with recovered cells through same 40 µM filter.
7.19.13 Sequentially repeat for each flask.
7.19.14 Centrifuge cells for 5 minutes at 200×g at room temperature.
7.19.15 Aspirate medium and resuspend each pellet in 5 mL Neurobasal medium.
NOTE: Store conicals at 4° C. until all vessels are processed.
7.19.16 Once all vessels have been processed, pool all cells and bring volume up to 200 mL total.

7.19.17 Perform cell count:
  7.19.17.1 Make a known dilution of cells in plain Neurobasal.
  7.19.17.2 Mix 20 uL of diluted cells with 20 uL of AOPI.
  7.19.17.3 Load 20 uL of cell/AOPI mixture onto Cellometer® slide.
  7.19.17.4 Insert the slide into Cellometer®.
  7.19.17.5 Choose the program file 'mDA Neurons AOPI'
  7.19.17.6 Provide a file name using the following format "DA01 Lot # MMDDYY d16 cryo"
  7.19.17.7 Enter the dilution value.
  7.19.17.8 Using the F1 channel, focus the cells using the knob on the right side of the machine.
  7.19.17.9 Once focused hit 'Count'
7.19.18 Record the total number of viable and non-viable cells/mL, total number of cells, and % viability.
7.19.19 Aliquot $3 \times 10^6$ cells into a cryotube labeled SSCRF-SOP-109 (cDNA production for QC).
7.19.20 Aliquot $3 \times 10^6$ cells into a cryotube labeled PT-OP-7020 (mycoplasma). Bring volume up to 1 mL with plain Neurobasal.
7.19.21 Aliquot $3 \times 10^6$ cells into a cryotube labeled MICR-CULT-SOP-1634 (sterility). Bring volume up to 1 mL, with plain Neurobasal.
7.19.22 Send tubes with separate operator for processing according to associated SOPS.
7.19.23 Cryopreserve the remaining cells according to SOP-SSCRF-105 (Cryopreservation of Day 16 Final Product).
7.19.24 Once done, rapidly remove cells from freezer and place into prelabeled boxes and load into shipper.
7.19.25 Transfer boxes to liquid nitrogen.
7.19.26 Record information into batch record.

Cells that were cryopreserved at day 16 were thawed and transplanted into lesioned rats (NIH nude, Taconic Biosciences, Inc.) (i.e., a Parkinsonian rat model). Amphetamine-induced rotational behavior was examined in transplanted rats and sham transplanted rats before transplantation, and at 1, 2, 3, 4 and 5 months after transplantation. In vivo expression of hNCAM, and the mDA markers TH (tyrosine hydroxylase) and GIRK2 (G protein-activated inward rectifier potassium channel 2), was examined at five months post-transplant.

Cells that were cryopreserved at day 16 were thawed and transplanted into non-human primates. Fiber outgrowth from transplanted grafts and cellular morphology were examined six weeks post-transplant.

Results

As shown in FIG. 12, four months after transplantation of mDA precursors into lesioned rats, rats that received the transplants exhibited fewer rotations per minute compared to sham treated rats. At five months post-transplantation, immunocytochemistry analysis of the transplanted grafts showed that the grafts exhibited TH staining typical of mDA morphology, wherein the TH positive neurons were also positive for GIRK2 expression (FIG. 13).

The morphology of mDA precursor grafts transplanted into non-human primates was examined six weeks post-transplantation. The graft exhibited robust fiber outgrowth from the graft core, and also exhibited typical mDA morphology (FIG. 14).

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

What is claimed is:

1. An in vitro method for differentiating pluripotent stem cells comprising:
  (a) contacting a plurality of pluripotent stem cells with at least one inhibitor of TGFβ/Activin-Nodal signaling; and
  (b) contacting the cells with at least one activator of Sonic hedgehog (SHH) signaling, and at least one activator of wingless (Wnt) signaling to obtain a population of differentiated cells expressing forkhead box protein A2 (FOXA2) and LIM homeobox transcription factor 1 alpha (LMX1A), wherein the concentration of the at least one activator of Wnt signaling is increased during the contact with the cells, and
  wherein i) the concentration increase is initiated between about 2 days and about 6 days from the initial contact of the at least one activator of Wnt signaling with the cells and ii) the concentration of the at least one activator of Wnt signaling is increased by between about 250% and about 1800% of the initial concentration of the at least one activator of Wnt signaling contacted with the cells.

2. The method of claim 1, further comprising contacting the cells with at least one inhibitor of Bone morphogenetic protein (BMP) and Small Mothers Against Decapentaplegic (SMAD) signaling.

3. The method of claim 2, wherein the cells are contacted with the at least one inhibitor of TGFβ/Activin-Nodal signaling, the at least one inhibitor of BMP/SMAD signaling, and the at least one activator of SHH signaling for between about 4 days and about 10 days.

4. The method of claim 2, wherein the cells are contacted with the at least one inhibitor of TGFβ/Activin-Nodal signaling, the at least one inhibitor of BMP/SMAD signaling, and the at least one activator of SHH signaling for up to about 7 days, or for at least about 7 days.

5. The method of claim 2, wherein the at least one inhibitor of BMP and SMAD signaling comprises 4-(6-(4-(piperazin-1-yl)phenyl)pyrazolo[1,5-a]pyrimidin-3-yl)quinoline (LDN193189), Noggin, or a combination of the foregoing.

6. The method of claim 1, wherein the cells are contacted with the at least one activator of Wnt signaling for between about 8 days and about 15 days.

7. The method of claim 1, wherein the cells are contacted with the at least one activator of Wnt signaling for or up to about 12 days, or for at least about 12 days.

8. The method of claim 1, wherein the concentration of the at least one activator of Wnt signaling is increased about 4 days from its initial contact with the cells.

9. The method of claim 8, wherein the increase in the concentration of the at least one activator of Wnt signaling is between about 400% and about 1450% of the initial concentration of the at least one activator of Wnt signaling contacted with the cells.

10. The method of claim 9, wherein the increase in the concentration of the at least one activator of Wnt signaling is between about 700% and about 1050% of the initial concentration of the at least one activator of Wnt signaling contacted with the cells.

11. The method of claim 8, wherein the increase in the concentration of the at least one activator of Wnt signaling is an increase to a concentration of between about 3 μM and about 10 μM.

12. The method of claim 11, wherein the increase in the concentration of the at least one activator of Wnt signaling is an increase to a concentration of about 3 μM.

13. The method of claim 11, wherein the increase in the concentration of the at least one activator of Wnt signaling is an increase to a concentration of about 7.5 μM.

14. The method of claim 1, wherein the differentiated cells express at least one marker selected from the group consisting of tyrosine hydroxylase (TH), engrailed-1 (EN-1), and nuclear receptor related-1 protein (NURR1).

15. The method of claim 1, wherein the differentiated cells do not express detectable levels of paired box protein (PAX6) and/or Ki67.

16. The method of claim 1, wherein the method further comprises subjecting the population of differentiated cells to conditions favoring maturation of the cells into dopamine neurons.

17. The method of claim 16, wherein the conditions favoring maturation of the cells into dopamine neurons comprise contacting the cells with brain-derived neurotrophic factor (BDNF), glial cell-derived neurotrophic factor (GDNF), Cyclic adenosine monophosphate (cAMP), Transforming growth factor beta 3 (TGFβ3), ascorbic acid (AA), and/or DAPT.

18. The method of claim 1, wherein the pluripotent stem cells are selected from the group consisting of human nonembryonic stem cells, primate nonembryonic stem cells, rodent nonembryonic stem cells, human embryonic stem cells, primate embryonic stem cells, rodent embryonic stem cells human induced pluripotent stem cells, primate induced pluripotent stem cells, rodent induced pluripotent stem cells human recombinant pluripotent cells, primate recombinant pluripotent cells, and rodent recombinant pluripotent cells.

19. The method of claim 1, wherein the at least one activator of SHH signaling comprises a SHE protein, a Smoothened agonist, or a combination of the foregoing.

20. The method of claim 19, wherein the SHH protein comprises a recombinant SHH, a purified SHH, or a combination of the foregoing.

21. The method of claim 20, wherein the recombinant SHH comprises SHH C25II.

22. The method of claim 19, wherein the Smoothened agonist comprises purmorphamine.

23. The method of claim 1, wherein the at least one activator of Wnt signaling comprises CHIR99021, Wnt3A, Wnt1, or a combination of the foregoing.

24. The method of claim 1, wherein the pluripotent stem cells are differentiated into the differentiated cells expressing FOXA2 and LMX1A no later than between about 22 days and about 27 days from the initial contact of the pluripotent stem cells with the at least one inhibitor of TGFβ/Activin-Nodal signaling.

25. The method of claim 1, wherein the differentiated cells express a detectable level of CD142.

26. The method of claim 25, further comprising selecting cells expressing CD142.

27. The method of claim 1, wherein the at least one inhibitor of TGFβ/Activin-Nodal signaling comprises an inhibitor of TGFβreceptor.

28. The method of claim 27, wherein the inhibitor of TGFβreceptor comprises 4-[4-(1,3-benzodioxol-5-yl)-5-(2-pyridinyl)-1H-imidazol-2-yl]-benzamide (SB431542).

* * * * *